(12) United States Patent
Donaldson

(10) Patent No.: US 10,998,105 B2
(45) Date of Patent: May 4, 2021

(54) METHODS AND SYSTEMS FOR EVALUATION OF RISK OF SUBSTANCE USE DISORDERS

(71) Applicant: Prescient Medicine Holdings, Inc., Hummelstown, PA (US)

(72) Inventor: Keri Donaldson, Hummelstown, PA (US)

(73) Assignee: Prescient Medicine Holdings, Inc., Hummelstown, PA (US)

( * ) Notice: Subject to any disclaimer, the term of this patent is extended or adjusted under 35 U.S.C. 154(b) by 0 days.

(21) Appl. No.: 17/004,838

(22) Filed: Aug. 27, 2020

(65) Prior Publication Data
US 2021/0065909 A1    Mar. 4, 2021

Related U.S. Application Data

(60) Provisional application No. 62/892,212, filed on Aug. 27, 2019.

(51) Int. Cl.
*G16H 50/30* (2018.01)
*G16H 20/10* (2018.01)
*G16H 10/60* (2018.01)
*G16H 50/20* (2018.01)

(52) U.S. Cl.
CPC .............. *G16H 50/30* (2018.01); *G16H 10/60* (2018.01); *G16H 20/10* (2018.01); *G16H 50/20* (2018.01)

(58) Field of Classification Search
CPC ........ G16H 50/30; G16H 10/60; G16H 50/20; G16H 20/10
USPC .......................................................... 702/19
See application file for complete search history.

(56) References Cited

U.S. PATENT DOCUMENTS

| 2014/0012600 | A1 | 1/2014 | Domesek et al. |
| 2015/0379203 | A1 | 12/2015 | Douglass |
| 2016/0012180 | A1* | 1/2016 | Blum ................... C12Q 1/6883 506/2 |
| 2017/0206327 | A1 | 7/2017 | Heywood |
| 2018/0137235 | A1 | 5/2018 | Meshkin |
| 2019/0065674 | A1 | 2/2019 | Holland |

OTHER PUBLICATIONS

International Search Report and Written Opinion for PCT/US20/48184, dated Dec. 7, 2020.
Donaldson et al. "Multi-variant Genetic Panel for Genetic Risk of Opioid Addiction," Ann. Clin. Lab. Sci, Aug. 1, 2017 (Aug. 1, 2017), vol. 47, pp. 452-456.
De La Calleja et al. "Machine learning and image analysis for morphological galaxy classification," Mon. Not. R. Astron. Soc, Mar. 21, 2004 (Mar. 21, 2004), vol. 349, pp. 87-93.
Derrig et al. "Distinguishing the Forest from the TREES: A Comparison of Tree-Based Data Mining Methods," Variance, Jan. 31, 2008 (Jan. 31, 2008), vol. 2, pp. 184-208.
Krebs et al. "Effect of Opioid vs Nonopioid Medications on Pain-Related Function in Patients With Chronic Back Pain or Hip or Knee Osteoarthritis Pain: The SPACE Randomized Clinical Trial," JAMA, Mar. 6, 2018 (Mar. 6, 2018), vol. 319, pp. 872-882.
Lee et al. "Multinomial Logistic Regression Ensembles," J. Biopharmaceutical Statistics, Apr. 23, 2013 (Apr. 23, 2013), vol. 23, pp. 1-14.
Mittag et al. "Influence of Feature Encoding and Choice of Classifier on Disease Risk Prediction in Genome-Wide Association Studies," PLOS One, Aug. 18, 2015 (Aug. 18, 2015), vol. 10, e0135832, pp. 1-18.

* cited by examiner

*Primary Examiner* — Jerry Lin
(74) *Attorney, Agent, or Firm* — Womble Bond Dickinson (US) LLP

(57) ABSTRACT

Provided here are systems and methods for predicting risk of a substance use disorder and for providing decision support to healthcare professionals to implement a treatment regimen recommendation and mitigate any potential risk of a substance use disorder.

18 Claims, 11 Drawing Sheets

METHODS AND SYSTEMS FOR EVALUATION OF RISK OF SUBSTANCE USE DISORDERS

CROSS-REFERENCE TO RELATED APPLICATIONS

This application claims priority to and the benefit of U.S. Provisional Application No. 62/892,212, filed on Aug. 27, 2019, titled "Methods and Systems for Predicting Risk of Substance Use Disorders," the entire contents of which are incorporated herein by reference.

TECHNICAL FIELD

The present disclosure relates generally to the field of treating patients in response to evaluating a risk of substance use disorders. More specifically, the present disclosure relates to systems and associated methods for predicting risk of a substance use disorder and providing decision support for appropriate treatment regimens.

BACKGROUND

Substance abuse and dependence are defined collectively in the *Diagnostic and Statistical Manual of Mental Disorders,* 5th Edition (DSM-5) as substance use disorder (SUD). SUD is a medical condition in which an individual has a diminished ability to control the use of one or more legal or illegal substances. These substances include alcohol, cannabis, opioids, and nicotine. In a 2017 National Survey on Drug Use and Health, a substance use disorder involving the use of alcohol or illicit drugs in the past year affected approximately 19.7 million people (aged 12 or older). When these results were further parsed, about 14.5 million people had an alcohol use disorder and 7.5 million people who had an illicit drug use disorder. While drug use disorder involving marijuana affected 4.1 million people, opioid use disorder (OUD) involving prescription pain relievers or heroin affected about 2.1 million people. According to the Centers for Disease Control and Prevention (CDC), the number of deaths in the United States due to opioid overdose rose more than 10% from 42,249 in 2016 to 47,600 in 2017, with prescription opioid medications accounting for 35.8% of all opioid-related deaths in 2017. General trends from 2006 indicate that rates of opioid prescription have decreased, but an estimated 17.4% of the U.S. population filled at least 1 prescription in 2017 with the average person receiving 3.4 prescriptions. Additionally, misuse of these medications continues to be problematic, as an estimated 11.1 million individuals (12 years or older) misused prescription pain relievers in 2017, including hydrocodone, oxycodone, and fentanyl products.

Different strategies have been implemented to help alleviate this public health crisis, including publication of opioid prescribing guidelines by the CDC in 2016. There is some evidence that the guidelines have contributed to decreased prescription rates for high-dosage opioid medications and lower percentages of patients with overlapping opioid and benzodiazepine prescriptions. However, the CDC guidelines have had little effect on opioid overdose deaths, and have resulted in some unintended consequences, such as the abrupt discontinuation of opioid medications in patients who still need pain relief and the dismissal of patients from medical care. Moreover, several medical associations have raised concerns that efforts to limit opioid misuse and abuse have had a detrimental effect of unduly restricting pain management for patients with legitimate medical need for opioids, including those with cancer, cancer survivors, and others with debilitating chronic pain. These unintended consequences underscore the challenge of balancing the benefits of opioids for pain management and the risk of developing an opioid use disorder.

SUMMARY

Applicant recognized the problems noted above and has conceived and developed systems and associated methods for predicting risk of a substance use disorder and providing decision support for appropriate treatment regimens. Certain embodiments include methods for predicting risk of a substance use disorder using machine learning models and associated systems for providing decision support to healthcare professionals to implement a treatment regimen and mitigate the risk of the substance use disorder. Certain embodiments include methods and systems for determining health outcomes and/or healthcare resource utilization based on evaluating the risk of a substance use disorder using machine learning models. In certain embodiments, the systems and methods described herein are used by an insurance entity to provide insurance coverage for a treatment regimen. In certain embodiments, the systems and methods described herein are used by a prescription drug monitoring program (PDMP). These embodiments include storing an individual's risk of substance use disorders as part of the individual's medical records. A health care provider, such as a physician or a nurse or a pharmacist, can access the individual's risk of substance use disorder in the PDMP to inform their opioid prescribing or opioid dispensing decisions, and therefore can either protect an individual at risk by providing a non-opioid option or provide an opioid-regimen to an individual who would benefit from the opioid.

Embodiments include systems to determine a subject's risk for developing a substance use disorder. One such system includes the following components: (a) a SNP analyzer to analyze a sample from a patient and provide a first plurality of SNP profiles of each of a set of specified allelic variants in the sample; (b) a processor and a machine-readable storage medium storing (i) a trained ensemble model, the trained ensemble model being trained with inputs comprising a second plurality of SNP profiles associated with the specified set of allelic variants from a first plurality of test subjects and a third plurality of SNP profiles associated with the specified set of allelic variants from a second plurality of test subjects and outputs comprising a first plurality of substance use indicators specifying that the first plurality of test subjects have been diagnosed with the substance use disorder and a second plurality of substance use indicators specifying that the second plurality of test subjects have not been diagnosed with the substance use disorder, and (ii) instructions, when executed by the processor, are configured to provide the trained ensemble model with the first plurality of SNP profiles to generate a score indicative of risk to a substance use disorder for the patient based on the first plurality of SNP profiles; in response to the score based on the first plurality of SNP profiles being greater than a pre-determined threshold, transmit to a user interface an output indicating a predisposition of the patient to develop the substance use disorder; and in response to the score based on the first plurality of SNP profiles being less than or equal to the pre-determined threshold, transmit to the user interface an output indicating a lower likelihood of the patient to develop the substance use disorder. The system can further include a database storing a non-opioid based treatment regimen recommendation and an opioid-based treatment regimen recommendation. In an embodiment, the machine-readable storage medium further can include instructions to: in response to the score based on the first plurality of SNP profiles being greater than the pre-determined threshold, retrieve the non-opioid based treatment regimen recommendation from the database; and transmit to the user interface an output indicating the predisposition of the patient to develop the substance use disorder and the non-opioid based treatment regimen recommendation. In an embodiment, the machine-readable storage medium further can include instructions to: in response to the score based on the first plurality of SNP profiles being less than or equal to the pre-determined threshold, retrieve the opioid based treatment regimen recommendation from the database; and transmit to the user interface an output indicating the predisposition of the patient to develop the substance use disorder and the opioid based treatment regimen recommendation. In an embodiment, a treatment regimen recommendation can include a reduced dose of the opioid. In an embodiment, a treatment regimen recommendation can include a reduced dose of the opioid in combination with the non-opioid drug or other interventions. In an embodiment, a treatment regimen recommendation can include a limited time period for use of the opioid drug followed by extended use of the non-opioid drug or other interventions. For example, a treatment regimen recommendation can include use of an opioid drug for no more than 3 days, then use a non-opioid drug.

In an embodiment, the trained ensemble model includes two or more trained models. The trained ensemble model can be generated by at least one of a random tree model and a support vector machine model. In an embodiment, the sample is pre-processed prior to using the trained ensemble model. In an embodiment, the pre-processing includes ordinal encoding or one-hot encoding. A sample includes any information from a biological material, such as one or more of a SNP profile, other allelic variations, RNA expression data, or other genetic information.

An embodiment of a method of determining a subject's risk for developing a substance use disorder includes the step of analyzing a sample of the subject to obtain one or more SNP profiles of each of a set of specified allelic variants. In response to the one or more SNP profiles of each of the set of specified allelic variants, the method further includes determining, via a processor of a computing device and a trained ensemble model stored in a machine-readable storage medium of the computing device, a score indicating the subject's risk for developing a substance use disorder based on the one or more SNP profiles of each of the set of specified allelic variants. The method further includes determining, via the processor, a treatment regimen recommendation for the subject based on the score, and transmitting, via the processor, the score and the treatment regimen recommendation to a user device. In an embodiment, the score indicating the subject's risk for developing the substance use disorder is a value from the trained ensemble model between 0 and 1. In an embodiment, the trained ensemble model includes a pre-determined threshold, and the score being greater than the pre-determined threshold indicates the subject has a higher risk for developing the substance use disorder, and the score being less than or equal to than the pre-determined threshold indicates the subject has a lower risk for developing the substance use disorder. The computing device in this method can include a SNP analyzer to analyze the sample of the subject to obtain the one or more SNP profiles of each of a set of specified allelic variants. In an embodiment, the method further comprises the step of generating, via the processor, a report, the report including the treatment regimen recommendation and the score. In an embodiment, the method further comprises the step of transmitting, via the processor, the report to a state prescription drug monitoring program (PDMP) database. In an embodiment, the method further includes the following steps: prior to receipt of the sample, determining, via the processor, whether a prior determined score indicating the subject's risk for developing a substance use disorder is available for the subject; and in response to the determination that the prior determined score is not available for the subject, transmitting, via the processor of the computing device, a request for a sample of the subject; and in response to the determination that the prior determined score is available for the subject, determining, via the processor, a treatment regimen recommendation based on the prior determined score. In an embodiment, the prior determined score is stored in a patient record database containing electronic health records of the subject. In an embodiment, the set of specified allelic variants includes one or more of allelic variants of the following genes: serotonin 2A receptor, galanin, ATP binding cassette transporter 1, catechol-O-methyltransferase, dopamine transporter, dopamine D2 receptor, dopamine D1 receptor, methylene tetrahydrofolate reductase, dopamine beta hydroxylase, delta opioid receptor, a first mu opioid receptor (OPRM1), dopamine D4 receptor, gamma-aminobutyric acid, kappa opioid receptor, and a second mu opioid receptor (MUOR). In an embodiment, the set of specified allelic variants includes allelic variants of the following genes: serotonin 2A receptor, galanin, ATP binding cassette transporter 1, catechol-O-methyltransferase, dopamine transporter, dopamine D2 receptor, dopamine D1 receptor, methylene tetrahydrofolate reductase, dopamine beta hydroxylase, delta opioid receptor, a first mu opioid receptor (OPRM1), dopamine D4 receptor, gamma-aminobutyric acid, kappa opioid receptor, and a second mu opioid receptor (MUOR). In an embodiment, the determination of the score is further based on a subject's clinical data.

Embodiments also include a non-transitory machine-readable storage medium storing processor-executable instructions that, when executed by at least one processor, cause the at least one processor to perform the following steps: in response to receipt of a sample from a patient, determine if the sample contains a specified set of allelic variants; in response to a determination that the sample does not include the specified set of allelic variants, transmit a response to a user indicating that a score indicative of risk to a substance use disorder is not available. The instructions further cause the processor to perform the following: in response to a determination that the sample includes the specified set of allelic variants, determine a first plurality of SNP profiles for each of the specified set of allelic variants in the sample; and determine, using a trained ensemble model, a score indicative of risk to a substance use disorder for the patient based on the first plurality of SNP profiles for each of the specified set of allelic variants in the sample. The trained ensemble model is trained with inputs comprising a second plurality of SNP profiles associated with the specified set of allelic variants from a first plurality of test subjects and a third plurality of SNP profiles associated with the specified set of allelic variants from a second plurality of test subjects and outputs comprising a first plurality of substance use indicators specifying that the first plurality of test subjects have been diagnosed with the substance use disorder and a second plurality of substance use indicators specifying that the second plurality of test subjects have not been diagnosed with the substance use disorder. In an embodiment, the trained ensemble model includes two or more trained models. The trained ensemble model can be generated by at least one of a random tree model and a support vector machine model. In an embodiment, the sample is pre-processed prior to using the trained ensemble model. In an embodiment, the pre-processing includes ordinal encoding or one-hot encoding.

In an embodiment, the substance use indicators used in the trained ensemble model are a value between 0 and 1. In an embodiment, the instructions cause the processor to perform: in response to the score based on the first plurality of SNP profiles for each of the specified set of allelic variants in the sample being greater than 0.33, return an output indicating a predisposition to develop the substance use disorder. In an embodiment, the instructions cause the processor to perform: in response to the score based on the first plurality of SNP profiles for each of the specified set of allelic variants in the sample is less than or equal to 0.33, return an output indicating a lower likelihood to develop the substance use disorder. In an embodiment, the SUD includes one or more of an opioid use disorder, an alcohol use disorder, a cannabinoid use disorder, and a cocaine use disorder. In an embodiment, the clinical data of the patient is provided along with the sample. In an embodiment, the clinical data includes age, sex, race, and ethnicity. In an embodiment, the clinical data includes demographic data, socioeconomic data, and any data that about a subject that can be obtained by observation or oral or written communication.

Other aspects and features of the present disclosure will become apparent to those of ordinary skill in the art after reading the detailed description herein and the accompanying figures.

BRIEF DESCRIPTION OF DRAWINGS

The foregoing aspects, features, and advantages of the present disclosure will be further appreciated when considered with reference to the following drawings.

DETAILED DESCRIPTION

Figure 1A:
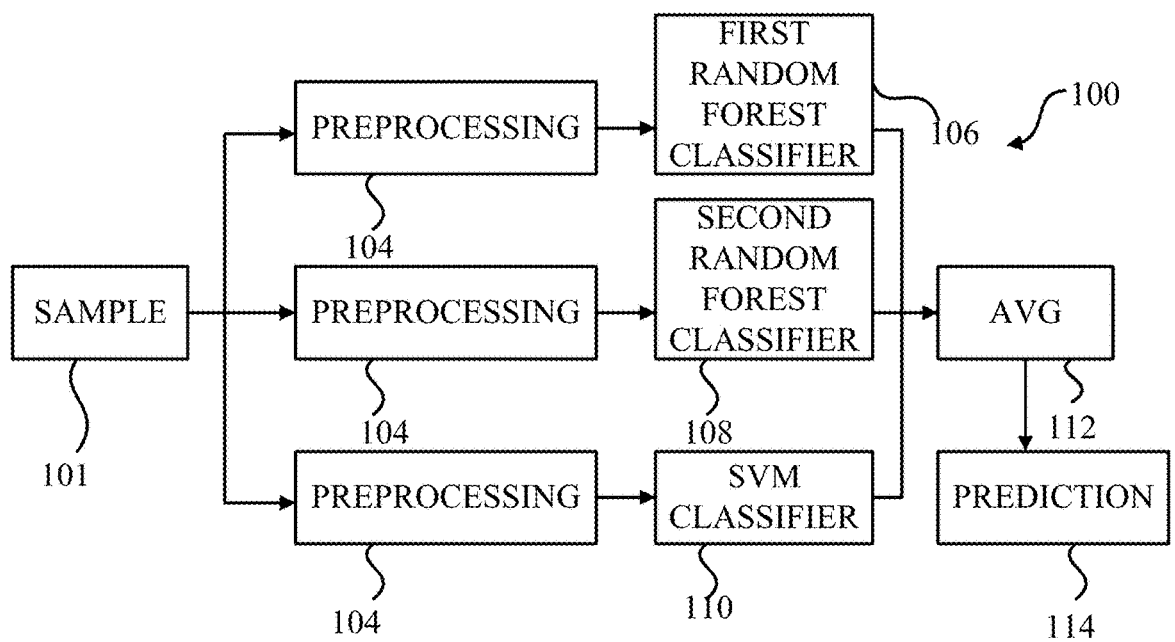
FIGS. 1A through 1E are diagrammatic representations of a stacked machine learning model, according to an embodiment of the present disclosure.

The foregoing aspects, features, and advantages of the present disclosure will be further appreciated when considered with reference to the following description of the embodiments and accompanying drawings. In describing the embodiments of the disclosure illustrated in the appended drawings, specific terminology will be used for the sake of clarity. The disclosure, however, is not intended to be limited to the specific terms used, and it is to be understood that each specific term includes equivalents that operate in a similar manner to accomplish a similar purpose. Numerous specific details, examples, and embodiments are set forth and described to provide a thorough understanding of various embodiments of the present invention. However, in certain instances, well-known or conventional details are not described in order to provide a concise discussion of embodiments of the present disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. Any examples of operating parameters and/or environmental conditions are not exclusive of other parameters/conditions of the disclosed embodiments. Additionally, it should be understood that references to "one embodiment", "an embodiment," "certain embodiments," or "other embodiments" of the present disclosure are not intended to be interpreted as excluding the existence of additional embodiments that also incorporate the recited features. Furthermore, reference to terms such as "above," "below," "upper," "lower," "side," "front," "back," or other terms regarding orientation are made with reference to the illustrated embodiments and are not intended to be limiting or exclude other orientations.

Embodiments include computer implemented methods for predicting risk of substance use disorders in a patient using a computer system having one or more processors coupled to a memory storing one or more computer readable instructions for execution by the one or more processors. One such method includes the steps of storing a set of data containing a plurality of subject records. The subject records can include clinical data of each of the subject, such as age, sex, race, prior medical history, and ethnicity. In an embodiment, the clinical data includes demographic data, socioeconomic data, and any data that about a subject that can be obtained by observation or oral or written communication. The subject records can also include data about health outcomes and healthcare resource utilization, such as quantification or description of the use of services by a subject for the purpose of preventing and curing substance use disorders or underlying disease, promoting maintenance of health and well-being, or obtaining information about one's health status and prognosis. For example, an increased risk of substance use disorder may include poorer health outcomes and greater utilization of healthcare resources. Each subject record includes a SNP (single nucleotide polymorphism) profile for each individual of a plurality of test subjects and subjects not diagnosed with a substance use disorder. Each subject record can also include a plurality of physical characteristics for each individual of a plurality of test subjects and subjects not diagnosed with a substance use disorder. The subject record for each of the plurality of test subjects also includes a first substance use indicator indicating that the test subject has been diagnosed with a substance use disorder. The subject record for each of the plurality of subjects not diagnosed with a substance use disorder includes a second substance use indicator indicating the subject has not been diagnosed with a substance use disorder. The method further includes the step of selecting a first subset of the subject records for the plurality of test subjects and a second subset of the subject records for the plurality of subjects not diagnosed with a substance use disorder. The first and second subsets do not include the first substance use indicator and the second substance use indicator, respectively. The first and second subsets serve as inputs into one or more initial machine learning models. The method further includes the step of determining whether the one or more initial machine learning models meet a predetermined sensitivity, a predetermined specificity, and a predetermined accuracy for predicting the first substance use indicator for the test subjects and the second substance use indicator of the subjects not diagnosed with a substance use disorder. The method further includes the step of generating an ensemble machine learning model responsive to the one or more initial machine learning models that meet the predetermined sensitivity, the predetermined specificity, and the predetermined accuracy. The method further includes the step of supplying a SNP profile of a patient to the ensemble machine learning model as an input to obtain a score indicative of the patient's risk of a substance use disorder. The method further includes the step of presenting the score or other indicator indicating the patient's risk of developing a substance use disorder to a healthcare professional for decision support to implement a treatment regimen and mitigate the patient's risk of substance abuse or substance dependence.

In another embodiment, a non-transitory machine-readable storage medium may be encoded with instructions executable by a processing resource. The non-transitory machine-readable storage medium includes instructions to store one or more sets of data. Each set of data may include one or more allelic variants. Each of the one or more allelic variants are associated with a subject. Each of the one or more allelic variants includes one or more SNP profiles of the subject and a value indicating whether the subject is diagnosed with a substance use disorder (SUD). The non-transitory machine-readable storage medium can include instructions to generate one or more subsets of data based on the sets of data. Each subset of data may include a plurality of SNP profiles. Each of the plurality of SNP profiles may include a same value indicating whether the subjects of the plurality of SNP profiles are diagnosed with SUD. The non-transitory machine-readable storage medium can include instructions to train a stacked model with training data generated via creation of the subsets of data. The stacked model may include, at least, a random forest model and a support vector machine model. Each training data may correspond to one of the one or more subsets of data. Each of the one or more subsets of data may correspond to the same value indicating whether the subject is diagnosed with SUD, such that the training of the stacked model provides a score or other indicator that informs a patient's risk of a substance use disorder.

In another embodiment, a non-transitory machine-readable storage medium may be encoded with instructions executable by a processing resource. The non-transitory machine-readable storage medium can include instructions to retrieve from memory, a trained stacked model. The stacked model may include, at least, a random forest model and a support vector machine model. The stacked model may be trained with one or more inputs and outputs derived from one or more sets of data. The one or more inputs may include one or more SNP profiles. Each of the one or more SNP profiles may be associated with one or more allelic variants of the subject. The one or more outputs may include a value indicating whether the subject has a risk of developing a SUD. The non-transitory machine-readable storage medium can include instructions to, in response to receipt of an input of a sample, determine if the sample includes the one or more alleles associated with the SNP profiles. The non-transitory machine-readable storage medium can include instructions to, in response to a determination that the sample does not include one of the one or more alleles associated with the SNP profiles, send a response to a user indicating that a prediction is not available. The non-transitory machine-readable storage medium can include instructions to, in response to a determination that the sample does include the one or more alleles associated with the SNP profiles, determine, using the retrieved trained stacked model and an average of the results of the random tree model and support vector machine model, a prediction of disposition to SUD relative to SNP profiles of the one or more alleles. A plurality of inputs to the retrieved trained stacked model may include all possible SNP profiles associated to the plurality of allelic variants.

Another embodiment of the disclosure is directed to a method of determining a subject's risk of developing a substance use disorder. This risk may be expressed as a score or a probability or other indicator that informs a patient's risk of a substance use disorder. In certain embodiments, the risk is presented as a binary determination, such as one of Yes or No or one of Low Risk or High Risk. In certain embodiments, the risk is presented as one of small set of possibilities, such as one of low risk, intermediate risk, or high risk. In certain embodiments, the risk is presented as a score ranging from 0 to 1 or from 0 to 100. The method includes the steps of receiving a sample of the subject; analyzing the sample, via a processor of a computing device, to obtain a SNP profile of each of a set of specified allelic variants. In response to the SNP profiles of each of the set of specified allelic variants, the method further includes the step of determining, via the processor and a trained stacked model of the computing device, a score indicating the subject's risk of developing a substance use disorder based on the SNP profiles of each of the set of specified allelic variants. The method further includes the step of determining, via the processor, a treatment regimen recommendation for the subject based on the score; and transmitting, via the processor, the score and treatment regimen recommendation to a user device.

In an embodiment, the score is a value output from the trained stacked model between 0 and 1 and the trained stacked model includes a pre-determined threshold. In an embodiment, the score with a value greater than the threshold indicates the subject has a high risk of developing a substance use disorder, and a score with a value less than or equal to the threshold indicates the subject has a low risk of developing a substance use disorder. In an embodiment, the set of specified allelic variants includes two or more of fifteen allelic variants. The fifteen allelic variants include allelic variants of the following genes: serotonin 2A receptor, galanin, ATP binding cassette transporter 1, catechol-O-methyltransferase, dopamine transporter, dopamine D2 receptor, dopamine D1 receptor, methylene tetrahydrofolate reductase, dopamine beta hydroxylase, delta opioid receptor, a first mu opioid receptor (OPRM1), dopamine D4 receptor, gamma-aminobutyric acid, kappa opioid receptor, and a second mu opioid receptor (MUOR). In an embodiment, the set of specified allelic variants includes all fifteen allelic variants.

The method may include transmitting, via one or more processors of a computing device, a request for a sample of the subject. The method may include determining, via the one or more processors, a treatment regimen recommendation for the subject based on the score and transmitting, via the one or more processors, the score and treatment regimen recommendation to a user device and to the subject's electronic medical records (EMR). In an embodiment, the score is a value output from the trained stacked model between 0 and 1 and the score with a value greater than the pre-determined threshold indicates the subject has a high risk of developing a substance use disorder, and a score with a value less than or equal to the pre-determined threshold indicates the subject has a low risk of developing a substance use disorder.

Another embodiment of the disclosure is directed to a system to determine a subject's risk of developing a substance use disorder. The system can include an analyzer with an input for a sample. In an embodiment, the analyzer conducts an allelic analysis of the sample received at the input to generate the SNP profiles for the trained ensemble model. The analysis, based on the received sample, may provide SNP profiles of each of a set of specified allelic variants. The system can include a trained ensemble model, such as a trained stacked model. The trained ensemble model may include one or more inputs and an output. The one or more inputs may accept one or more SNP profiles from the analyzer. Based on the SNP profiles, the trained ensemble model may provide, at the output, a score or other indicator that informs a patient's risk of a substance use disorder. The system may include a user interface input/output in communication with a processor and machine-readable storage medium. The machine-readable storage medium may store instructions and the instructions may be executable by the processor. The executed instruction may, in response to a risk output from the trained ensemble model, determine an indicator to indicate a subject's risk of developing substance use disorder, the indicator based on the risk or probability. Further, the instructions may include transmission of the indicator to a user interface associated with a user device.

The embodiments described herein may utilize a trained ensemble or trained stacked model to determine a predicted predisposition to a substance use disorder of a subject. This approach may allow for prevention or modification of prescription of specific medications to individuals predisposed to a substance use disorder, thus preventing potential dependence or addiction through prescription. For example, upon receipt of a sample, a system may provide a prediction of the likelihood of a patient developing a substance use disorder within, depending on various factors, hours or days. Certain embodiments include methods and systems for determining health outcomes and/or healthcare resource utilization based on evaluating the risk of a substance use disorder using machine learning models. For example, an increased risk of substance use disorder may include poorer health outcomes and greater utilization of healthcare resources. Certain embodiments include methods and systems for determining health or wellness of the subject based on the analysis of the allelic variants and/or clinical data of the subject. Certain embodiments include methods and systems for determining health outcomes of the subject based on the analysis of the allelic variants and/or clinical data of the subject. Certain embodiments include methods and systems for determining healthcare resource utilization by a subject based on the analysis of the allelic variants and/or clinical data of the subject.

Figure 2A:
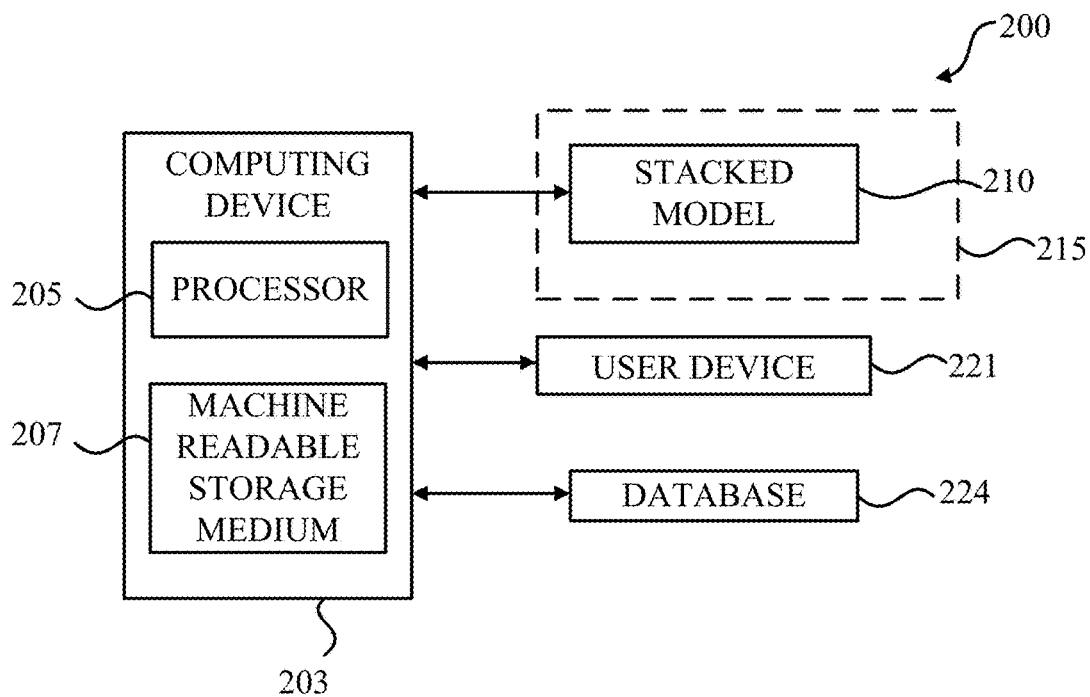
FIGS. 2A through 2C are diagrammatic representations of systems containing a stacked machine learning model, according to an embodiment of the present disclosure.
Figure 2B:
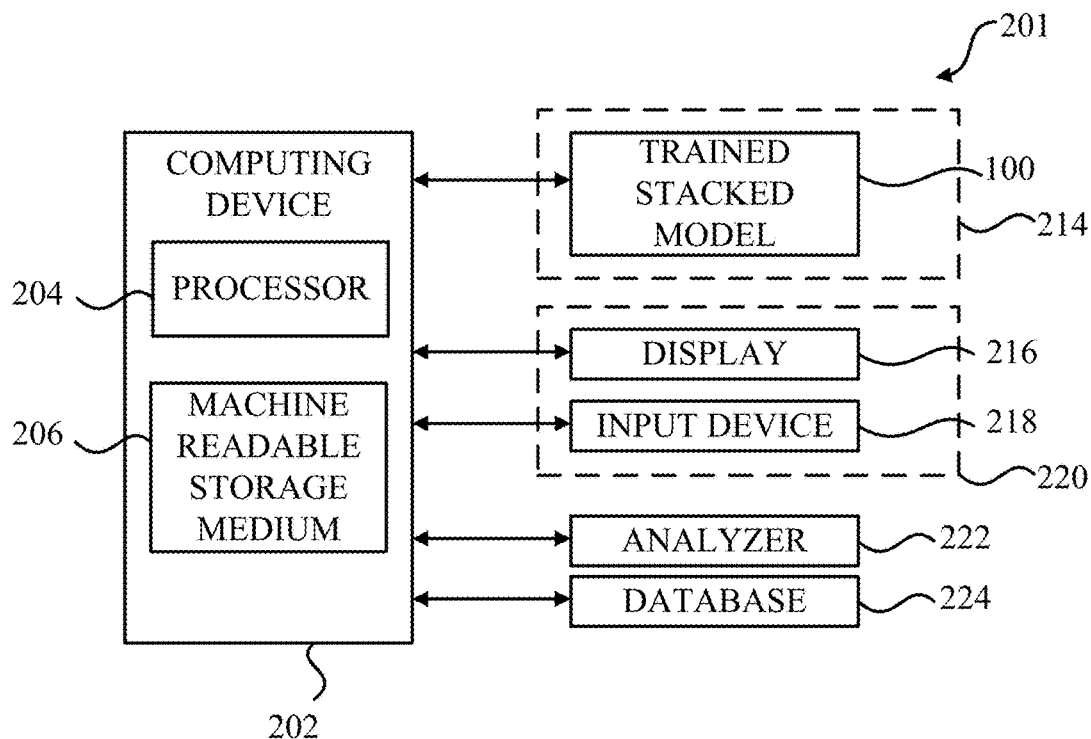
Figure 2C:
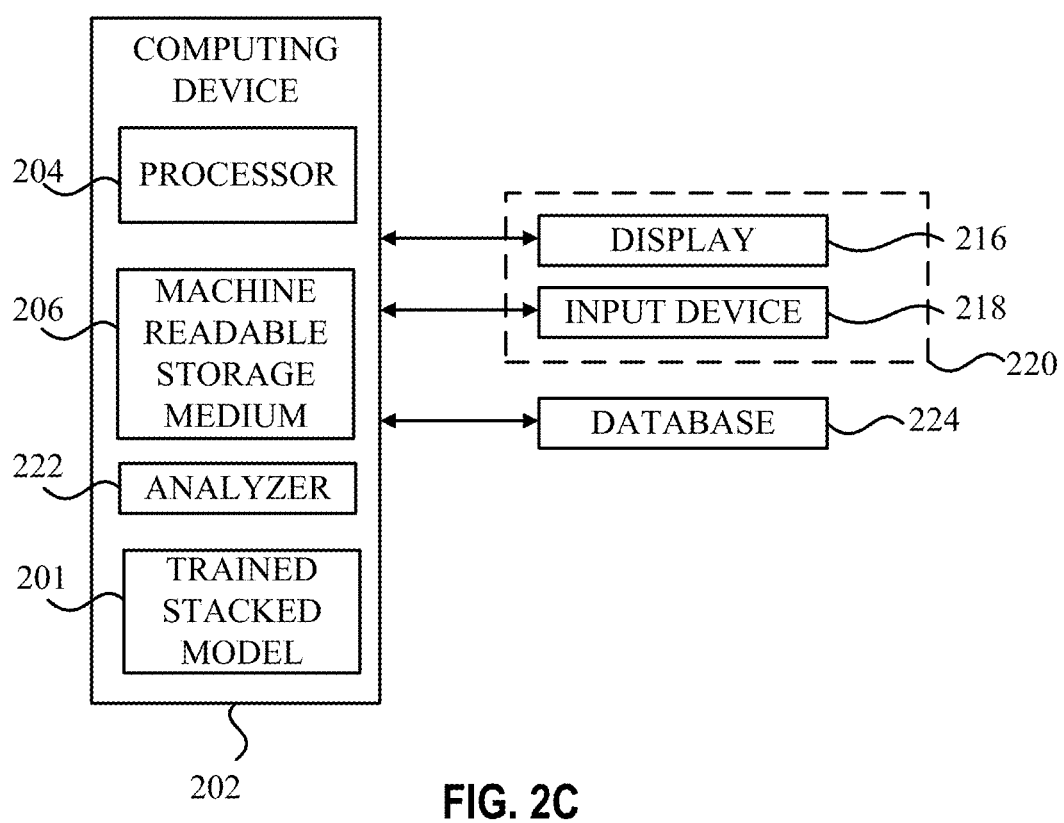

In an embodiment, a system 201 (as illustrated in FIGS. 2B, and 2C) for predicting risk of substance use disorders and/or for providing decision support to healthcare professionals to implement a treatment regimen and mitigate substance use includes a user device 220, an electronic communications network, a SNP analyzer 222, a patient record database 224, a processor 204 to execute instructions stored on a non-transitory machine readable storage medium 206, the instructions to, when executed by the processor 204, may retrieve and/or utilize a trained ensemble and/or trained stacked model 100 stored in a memory 214 (e.g., the computing device 202 may receive or retrieve the trained stacked model 100 and store the trained stacked model 100 in the machine readable storage medium 206). In an embodiment, the system 201 for predicting risk of substance use disorders can include decision support modules (for example, included as machine readable instructions stored in machine readable storage medium 206) coupled to a patient record database 224 and/or one or more of a prescription drug database, the patient's electronic health records, and drug utilization records. Decision support modules may include providing evidence-based information to the healthcare professional regarding drug selection and dosing, potential adverse drug reactions and drug allergies, duration or form of prescribed drugs, or stratification of treatments. The computing device 202 may include an input/output to connect to a user device 220 or user interface. The user device 220 or user interface may include a display 216. The display 216 may be configured to display a graphical user interface (GUI) for receiving a SNP profile and one or more electronic medical records (EMR) or electronic health records (EHR) associated with a patient and displaying a risk of a substance use disorder. The GUI may display one or more recommendations for treatment regimens for the patient. The electronic communications network is in communication with the user device 220, the SNP analyzer 222, the patient record database 224, and the processor 204 that executes the trained ensemble and/or trained stacked model 100. In another example as shown in FIG. 2C, the computing device 202 may be or include a SNP analyzer 222 or another genetic information analyzer. Further, rather than connect to the trained stacked model 100, the computing device 202 can include the trained stacked model 100 (e.g., the trained stacked model 100 may be stored in the machine-readable storage medium 206).

In an embodiment, a system 200 (as illustrated in FIG. 2A) may include a computing device 203 including a machine-readable storage medium 207 and a processor 205. The machine readable storage medium 207 includes instructions, when executed by the processor 205, to receive a plurality of SNP profiles and/or substance use disorder profiles associated to the plurality of test subjects and subjects not diagnosed with a substance use disorder from the user device 221 or patient record database 224, train one or more predictive machine learning models (for example, stacked model 210 or a first random forest model 105, second random forest model 107, and a SVM model 109) using the plurality of physical characteristics and associated SNP profiles, thereby generating an ensemble predictive model (for example, a trained stacked model 100) for determining risk of substance use disorder. The machine-readable storage medium 207 may include instructions, when executed by the processor 205, to receive a plurality of physical and/or clinical data from a plurality of EMR associated to a plurality of test subjects and subjects not diagnosed with a substance use disorder from a user device 221 or patient record database 224. The machine-readable storage medium 207 may also include instructions to retrieve one or more treatment regimen recommendations associated with a particular risk of substance use disorder. The data (as in, the training data 102) used to train the one or more predictive machine learning models (e.g., a stacked model 210) may include a substance use disorder profile. The substance use disorder profile may include one or more of a plurality of physical or clinical data from a plurality of EMR associated to a plurality of test subjects and subjects not diagnosed with a substance use disorder, a plurality of SNP profiles associated to the plurality of test subjects and subjects not diagnosed with a substance use disorder, a plurality of medical diagnoses regarding substance use disorders associated to the plurality of test subjects and subjects not diagnosed with a substance use disorder, and/or a plurality of treatment regimen recommendations.

The machine-readable storage medium 207 may include instructions to assign a plurality of weight values to the training data 102 within a plurality of substance use disorder profiles, such as to a plurality of associated SNP profiles of the training data, determine the one or more weighted data inputs of the training data, thereby to form an initial set of decision making rules. The machine-readable storage medium 207 may include instructions to compare the initial set of decision-making rules to the one or more weighted data inputs of the training data and re-weight the initial set of decision-making rules based on the comparison to create a re-weighted set of decision-making rules. The re-weighted set of decision-making rules and the one or more weighted data inputs of the training data may be used to update the initial predictive model to generate an ensemble predictive model for determining risk of substance use disorder.

Figure 1B:
Figure 1C:
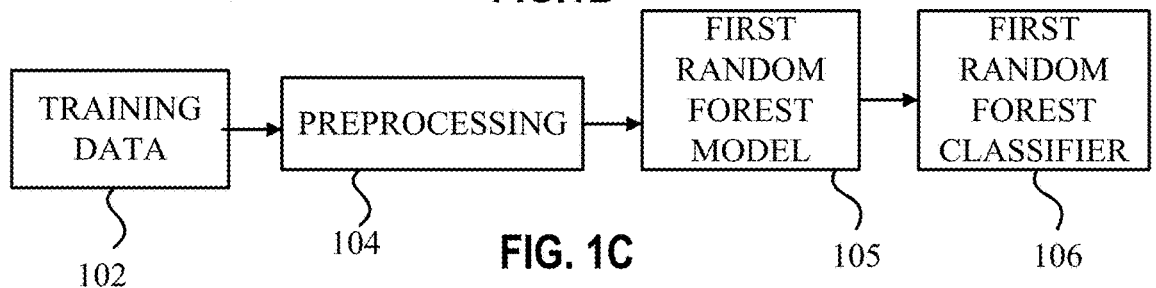
Figure 1D:
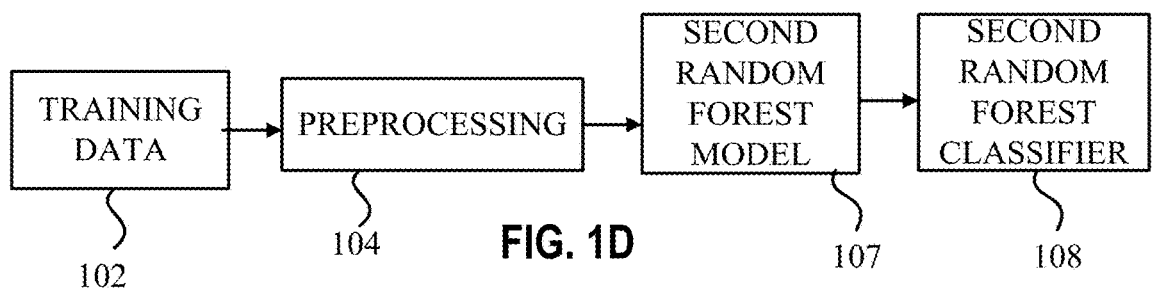
Figure 1E:
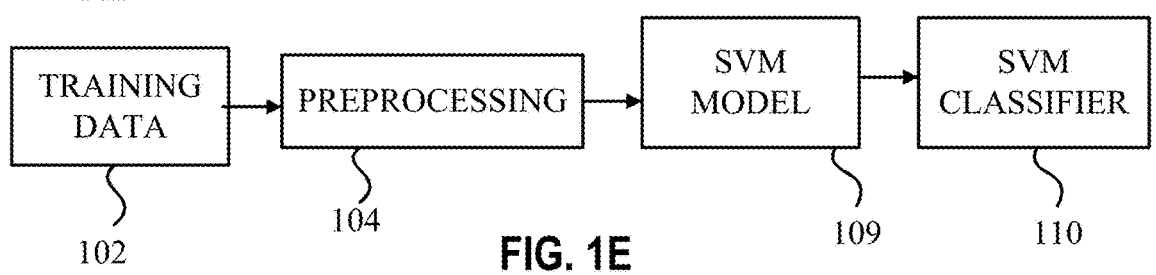

For example, the training data 102 may be comprised of a set of data (as illustrated in FIG. 1B) including data associated with a group of individuals or subjects known to have a substance use disorder and a group of individuals or subjects with no known substance use disorders. Various models may be utilized to create a classification, prediction, or probability of developing substance use disorder, based on SNP profiles and/or physical and/or clinical data. Models and methods may include decision trees, random forest models, random forests utilizing bagging or boosting (as in, gradient boosting), neural network methods, support vector machines (SVM), other supervised learning models, other semi-supervised learning models, and/or other unsupervised learning models, as will be readily understood by one having ordinary skill in the art. Further, a stacked model 210 or an ensemble machine learning model may be utilized. A stacked model 210 may include two or more learning models, for example, a first random forest model 105, a second random forest model 107, a SVM model 109, and/or other models as will be readily understood by one having ordinary skill in the art.

As illustrated in FIGS. 1A and 1C through 1E, the trained stacked models 100 may include a first random forest classifier 106 based on results from a first random forest model 105, a second random classifier 108 based on a second random forest model 107, and a SVM classifier 110 based on a SVM model 109. The first random forest model 105 and second random forest model 107 may be trained utilizing a re-sampling or bootstrapping technique. In other words, samples from the training data 102 may be re-used or left out for new decision trees or sets of decision trees. As illustrated in FIG. 1B, the training data 102 may include an 80% training 116 and 20% testing 118 split (other split percentages, such as 70/30 may be utilized, as will be readily understood by one having ordinary skill in the art). In other words, the random forest may be trained with the 80% 116 of the training data 102, while the 20% 118 of the training data 102 may be held out for testing the newly trained model. In another example, the stacked model 210 may include a gradient boosted tree model. The gradient boosted tree model may include similar training methods. The gradient boosted tree model may include logic that measures error based on small changes to predictions. In other words, the target outcome for each case may depend on how changing a case's prediction impacts prediction error. Other models may be utilized, for example, linear regression models, logistic regression models, naïve Bayes models, kNN models, k-Means models, dimensionality reduction models, other gradient boosting models, and/or neural networks, as will be readily understood by one having ordinary skill in the art. In another example, ensemble model training may utilize n fold cross-validation. In other words, the set of data may be split n times (for example, 5 fold or 20 fold cross-validation). While each split trains a model, another split may be leftover. The trained model may test against the leftover split. The model may be trained again, but a different split may be held out for testing. This may occur until all the training data 102 is utilized for training and testing. Such a training and testing method may prevent or lessen the likelihood of over-fitting. Over-fitting may occur when a model exhibits random error or noise instead of an underlying relationship. As noted, cross-validation may prevent or lessen the likelihood of over-fitting. Other methods to avoid over-fitting may be utilized, as will be readily understood by one having ordinary skill in the art.

Training a model, may result in a classifier, predictor, score, or probability. A sample 101 (for example, a SNP profile obtained from a biological material, such as from a buccal swab or a blood sample (or other method of obtaining DNA or RNA), other allelic variations, RNA expression data, and/or physical or clinical data may be entered via an input device 218 and/or a SNP analyzer 222 into a computing device) may be applied to the predictor to produce a probability or prediction score 114 between 0 and 1 or some other arbitrary numerical range. Multiple models or ensemble models may be stacked to further prevent over-fitting or over confident predictions. The average 112 of multiple models may, when those models disagree, tend to average out towards a mean of the original dataset.

As noted, the machine readable storage medium 206 may include instructions to determine risk or probability of development of substance use disorder for a particular patient using the trained ensemble and/or trained stacked model 100 responsive to the plurality of physical or clinical data and/or the associated SNP profile of the particular patient, identify the one or more associated recommendations responsive to the risk of substance use disorder, and transmit the risk of substance use disorder and the one or more associated treatment regimen recommendations to the user device 220 via the electronic communication network to be displayed on the GUI. This risk may be expressed as a score or a probability or other indicator that informs a patient's risk of a substance use disorder. In certain embodiments, the risk is presented as a binary determination, such as one of Yes or No or one of Low Risk or High Risk. In certain embodiments, the risk is presented as one of small set of possibilities, such as one of low risk, intermediate risk, or high risk. In certain embodiments, the risk is presented as a score ranging from 0 to 1 or from 0 to 100. The user device 220 may be configured to display a GUI for displaying the risk of substance use disorder and the one or more associated treatment regimen recommendations. For example, the user device 220 may include a mobile device (e.g. smart phone, tablet, etc.), a desktop computer, a laptop, a wearable computing device, or other type of computing device, as will be readily understood by one having ordinary skill in the art. The user device 220 may further include a mobile computer application.

As noted, the output of each of the models may be a value from 0 to 1 or some other arbitrary number. As noted, an average of the outputs may be taken, as a correction for potential disagreements in the models. In a further example, an allocated threshold may indicate predisposition to develop substance use disorder, such as an output greater than 0.33, while a value less than or equal to 0.33 may indicate no or lower likelihood or predisposition to develop substance use disorder. Further, the allocated threshold may be set during the training of the stacked model 210. For example, the machine-readable storage medium 207 may include instructions to automatically set the allocated threshold or include a predetermined value for a threshold. In another example, various indicators may be associated with various thresholds. For example, an indicator may include, "YES", "NO", "LOW", "HIGH", "INTERMEDIATE", some other indicator to indicate level of risk associated with substance use disorder, and/or some combination thereof. Further, "YES" may indicate that a patient is predisposed to develop substance use disorder, while "NO" may indicate that the patient is not predisposed to develop substance use disorder. "LOW" may indicate that a patient has a low risk of substance use disorder, "INTERMEDIATE" may indicate that a patient has a level of risk somewhere in between "HIGH" and "LOW" (but not past a threshold to indicate a high risk or low risk), and "HIGH" may indicate that a patient has a high level of risk of substance use disorder. In another example, the indicator may be presented, via the user device 220, with or without the percentage of risk (in other words, the output of the average of the trained stacked model 100).

In an embodiment, the machine-readable storage medium further can include instructions the processor to: in response to the score that informs a patient's risk of a substance use disorder being greater than the pre-determined threshold, retrieve the non-opioid based treatment regimen recommendation from the database; and transmit to the user interface an output indicating the predisposition of the patient to develop the substance use disorder and the non-opioid based treatment regimen recommendation. In an embodiment, the machine-readable storage medium further can include instructions to: in response to the score that informs a patient's risk of a substance use disorder being less than or equal to the pre-determined threshold, retrieve the opioid based treatment regimen recommendation from the database; and transmit to the user interface an output indicating the predisposition of the patient to develop the substance use disorder and the opioid based treatment regimen recommendation. In an embodiment, a treatment regimen recommendation can include a reduced dose of the opioid. In an embodiment, a treatment regimen recommendation can include a reduced dose of the opioid in combination with the non-opioid drug or other interventions. In an embodiment, a treatment regimen recommendation can include a limited time period for use of the opioid drug followed by extended use of the non-opioid drug or other interventions. For example, a treatment regimen recommendation can include use of an opioid drug for no more than 3 days, then use of a non-opioid drug.

The present disclosure also discloses embodiments directed to a method for predicting a patient's risk of developing a substance use disorder or for providing decision support to healthcare professionals to implement a treatment regimen on a graphical user interface (GUI) of a computing system using an ensemble or stacked machine learning model. In an example, training data 102 or the sample 101 may be pre-processed by a pre-processing module 104 or pre-processing instructions stored on the computing device 203 and/or computing device 202, respectively, or at the memory 215 where the stacked model 210 is stored or the memory 214 where the trained stacked model 100 is stored. In one such method, a plurality of physical or clinical data and associated SNP profile of a particular patient may be processed to a format for processing, such as normalization, one-hot encoding, and/or ordinal encoding, by one or more machine learning models, and storing the plurality of physical data and associated SNP profile of the particular patient to a data structure in a patient records database 224. The method may further include training one or more initial predictive models for predicting a patient's risk of developing a substance use disorder using the plurality of physical or clinical data and/or associated SNP profile of a plurality of subjects (with and without diagnoses of substance use disorder) constituting the training data 102, thereby generating an updated predictive model for predicting risk of substance use disorders or for providing decision support to healthcare professionals to implement a treatment regimen. The method may additionally include assigning a plurality of weight values to the one or more data inputs of the training data 102, determining the one or more weighted data inputs of the training data 102, thereby to form an initial set of decision making rules, and comparing the initial set of decision making rules to the one or more weighted data inputs of the training data 102. In an embodiment, the clinical data includes age, sex, race, and ethnicity. In an embodiment, the clinical data includes demographic data, socioeconomic data, and any data that about a subject that can be obtained by observation or oral or written communication.

Further, the method may include, for example, re-weighting the initial set of decision-making rules based on the comparison to create a re-weighted set of decision-making rules. The re-weighted set of decision-making rules and the one or more weighted data inputs of the training data may be used to update the initial predictive model to generate the updated predictive model for predicting risk of substance use disorders or for providing decision support to healthcare professionals to implement a treatment regimen.

An embodiment of the method includes the step of checking a PDMP to determine if a patient's risk of developing a substance use disorder has been determined by the methods described herein. In an embodiment, the PDMP is consulted by a user, such as a doctor or pharmacist or other healthcare professional, for a patient who is prescribed a particular drug (e.g., a pre-op team for a patient who has chosen an elective surgery or a doctor prescribing an opioid). If the PDMP records indicate that the patient has been evaluated for his/her risk of developing a substance use disorder, then the drug prescription is provided in response to his/her risk of developing a substance use disorder. For example, a non-opioid option is provided to the patient if his/her risk of developing a substance use disorder is high. Or, an opioid regimen is provided to an individual who would benefit from the opioid regimen and has a low risk of developing a substance use disorder. If the patient has not been evaluated for his/her risk of developing a substance use disorder, then the methods include the steps of collecting a sample from the patient and evaluating the patient's risk of developing a substance use disorder. If the patient's risk is high, then a healthcare provider or a pharmacist reviews the results with the patient and a treatment regimen is developed. The patient is offered a limited opioid prescription, such as one to last less than three days, or is provided with non-opioid alternatives. The method also includes updating the PDMP records with the patient's risk of developing a substance use disorder and the resulting treatment regimen. An opioid regimen includes one or more of a prescription opioid, such as hydrocodone, oxycodone, oxymorphone, morphine, codeine, or fentanyl. Non-opioid alternatives or non-opioid treatment regimens can include drug-based and/or non-drug-based options. Drug-based options include disease-specific treatments when available (e.g., triptans for migraines or gabapentin/pregabalin/duloxetine for neuropathic pain), interventional therapies (e.g., corticosteroid injections or nerve blocks), acetaminophen, non-steroidal anti-inflammatory drugs, tricyclic antidepressants, serotonin/norepinephrine reuptake inhibitors, or topical agents (lidocaine or capsaicin). Examples of non-drug-based options, include acupuncture, chiropractic approaches, osteopathic manipulative treatment, massage therapy, electrical nerve stimulation, occupational therapy, and physical therapy.

In an embodiment, an insurance payor can access a PDMP to determine if a patient's risk of developing a substance use disorder has been determined by the methods described herein. If the patient has been evaluated for his/her risk of developing a substance use disorder, then insurer authorizes coverage of a drug prescription in response to his/her risk of developing a substance use disorder. For example, a non-opioid option is provided to the patient if his/her risk of developing a substance use disorder is high. Or, an opioid regimen is provided to an individual who would benefit from the opioid regimen and has a low risk of developing a substance use disorder. If the patient has not been evaluated for his/her risk of developing a substance use disorder, then the insurance payor requests processing a sample from the patient and evaluating the patient's risk of developing a substance use disorder. If the patient's risk is high, then the payor informs the patient's healthcare provider or pharmacist to review the results with the patient and develop a treatment regimen. The patient is offered a limited opioid prescription, such as one to last less than three days, or is provided with non-opioid alternatives. The method also includes updating the PDMP records with the patient's risk of developing a substance use disorder and the resulting treatment regimen. In an embodiment, the insurance company requests an evaluation of the patient's risk of developing a substance use disorder be performed in the context of a coverage determination (i.e., whether the insurance company will pay for whatever medication therapy is selected).

FIGS. 3A through 3E illustrate flow diagrams, implemented in a computing device, to predict a subject's or patient's predisposition to substance use disorder (in other words, a patient's risk of developing a substance use disorder), according to an embodiment. The method is detailed with reference to the computing device 202. The actions of methods 300, 322, and 342, may be completed by the computing device 202. Specifically, methods 300, 322, and 342 may be included in one or more programs, protocols, or instructions loaded into the machine-readable storage medium 206 of the computing device 202 and executed on the processor 204 or one or more processors of the computing device 202. The order in which the operations are described is not intended to be construed as a limitation, and any number of the described steps may be combined in any order and/or in parallel to implement the methods.

Figure 3A:
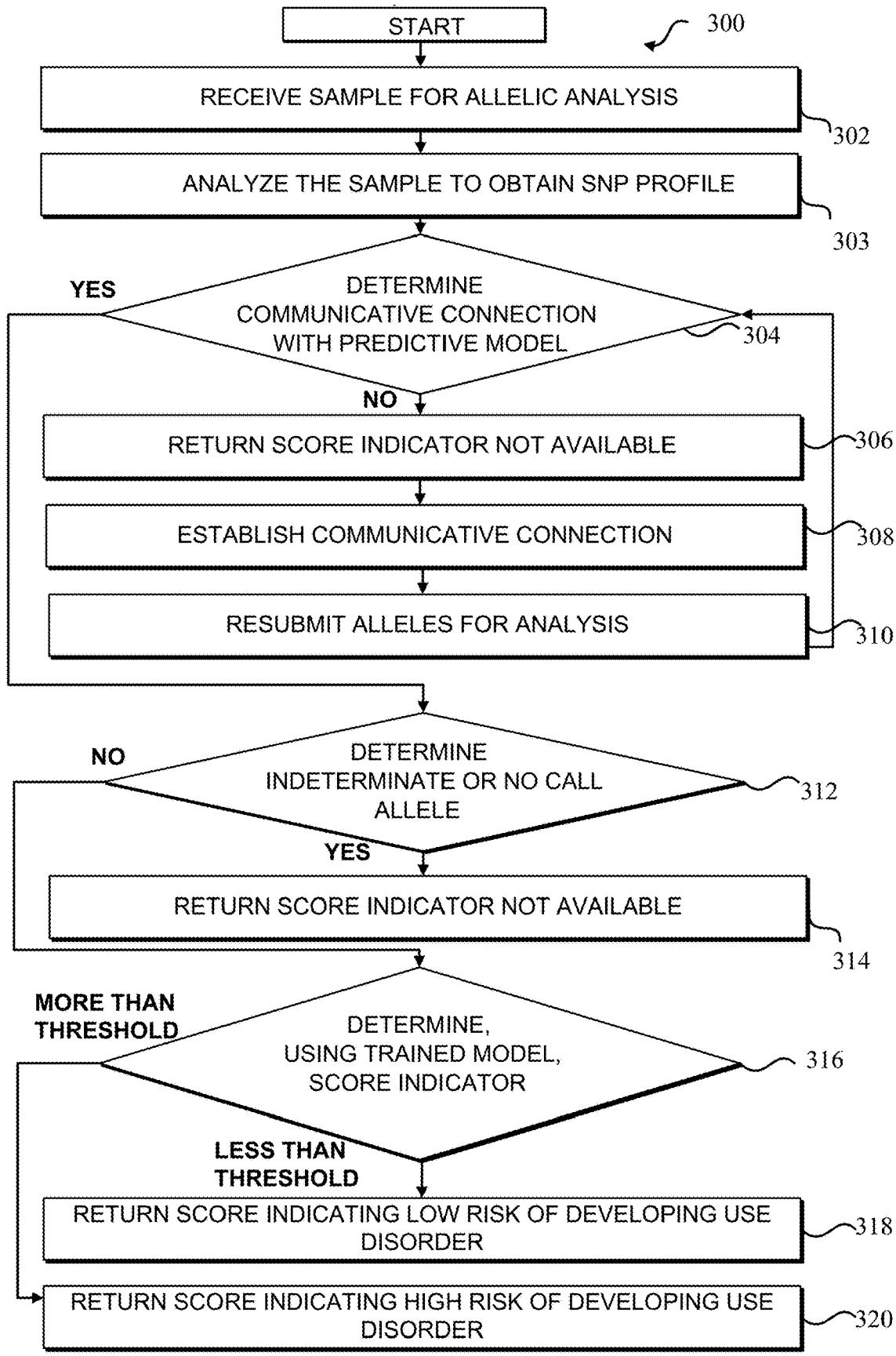
FIGS. 3A through 3E are flowcharts of different embodiments of methods of predicting risk of substance use disorders.
Figure 3B:
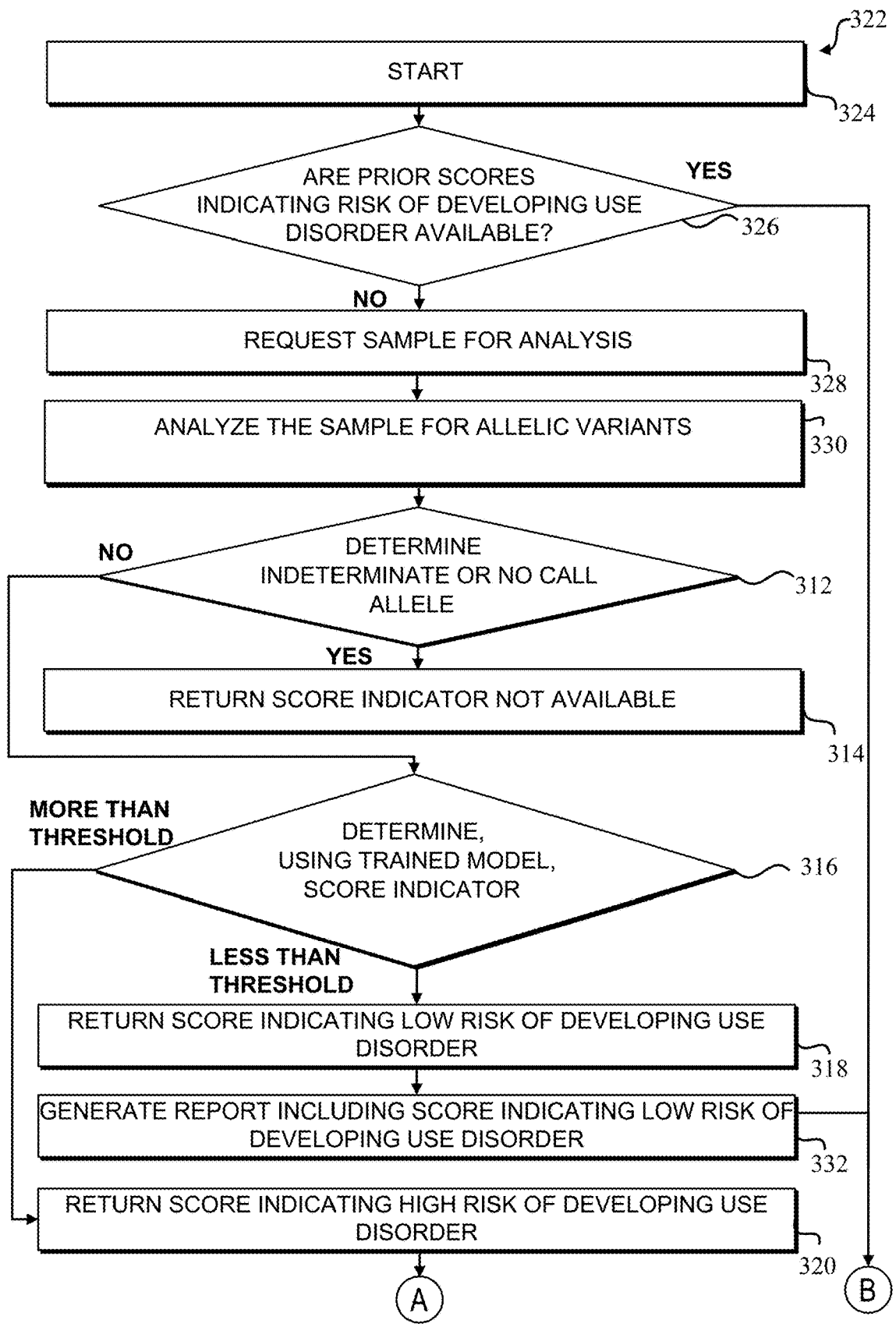
Figure 3C:
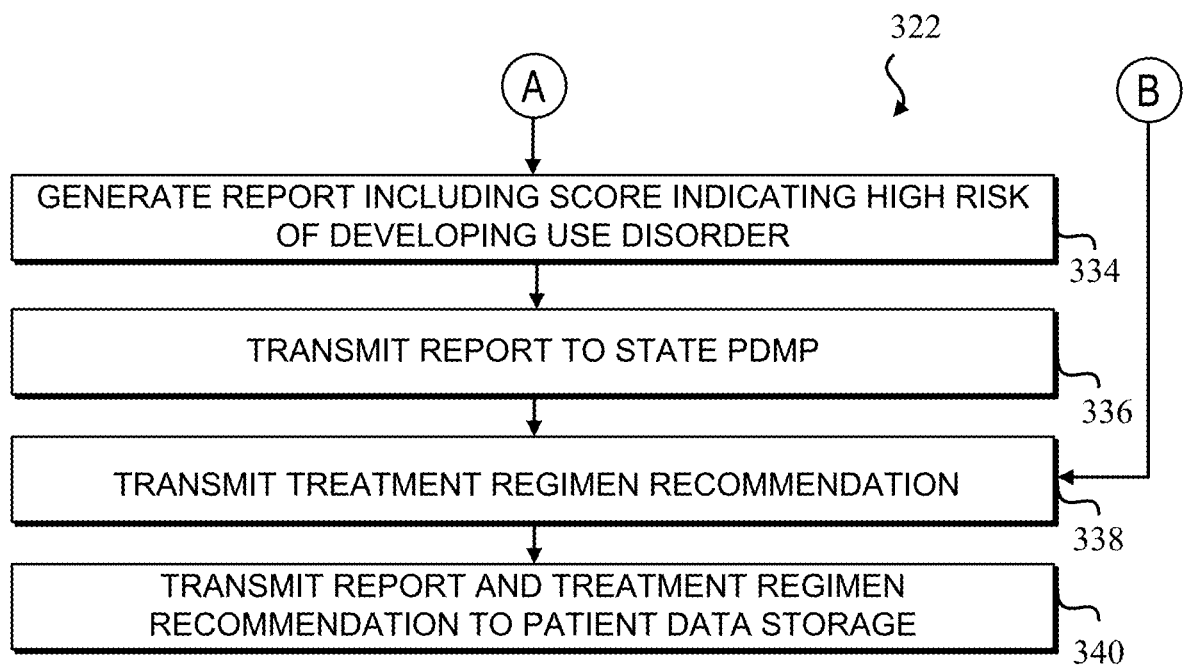

FIG. 3A illustrates a flowchart of a method 300 to utilize a stacked machine learning model to predict a subject's or patient's predisposition to substance use disorder (in other words, a patient's risk of developing a substance use disorder), according to an embodiment. The method 300, at step 302, may include receiving a sample for allelic analysis (e.g., such as from a buccal swab, a blood sample and/or any other sample containing genetic material). The sample is analyzed for one or more SNP profiles associated to a specified set of allelic variants of the subject or patient. In an example, the sample is analyzed for one or more allelic variants (for example, the 15 allelic variants shown in Table 2 below). Information from a biological material or a sample 101 may be entered into a computing device 202 via an input device 218. The input device 218 may be a keyboard, touchscreen, and/or mouse. In another example, a SNP analyzer 222 may send the SNP profiles to the computing device 202 (for example, from the analysis of a buccal swab). In yet another example, the computing device 202 may include the SNP analyzer 222 or other analyzer to obtain genetic information from a biological material.

In such examples, in response to the receipt of a sample, at step 303, the computing device 202, via the included SNP analyzer 222, may analyze the sample to obtain the one or more SNP profiles of the allelic variants (or other genetic information) from the sample. In an embodiment, the SNP analyzer can include any automated DNA or RNA sequencing system coupled to a software module to call SNPs in genome or transcriptome samples. In an embodiment, data from a next generation sequencing system or high density SNP arrays are aggregated and aligned to call the SNPS of the set of specified allelic variants.

The method 300, at step 304, may include, in response to receipt of the sample, determining whether the computing device 202 is communicatively connected to the trained ensemble or trained stacked model 100. If the computing device 202 is not connected to the trained ensemble or trained stacked model 100, the computing device 202 may, at step 306, send a prompt to a healthcare professional that an initial risk, prediction, or score of substance use disorder is not available. After sending the prompt, the computing device 202 may, at step 308, attempt to re-establish connection with the trained ensemble or trained stacked model 100. In another example, the computing device 202 may not send a prompt, but rather attempt to re-establish connection with the trained ensemble or trained stacked model 100, which may take a short period of time (e.g., seconds or minutes). After attempting to re-establish the connection, the method, at step 310, may restart the process with the same sample (for example, by resubmitting the one or more allelic variants for analysis to the computing device 202). In another example and as illustrated in FIG. 2C, the computing device 202, rather than connecting to the trained stacked model 100, may include the trained stacked model (e.g., the trained stacked model 100 may be stored in either the machine-readable storage medium 206 or another memory of the computing device 202). Thus, the computing device 202 may not check for a communicative connection.

The method 300, at step 312, may include determining, via the computing device 202, whether the sample includes the one or more allelic variants used to train the trained ensemble or trained stacked model 100 (e.g., specified allelic variants). In response to a determination, at step 312, that not all the one or more allelic variants are present (for example, due to an indeterminate allele or no call), the method 300, at step 314, may include prompting, via the computing device 202 to the user device 220 or display 216, a healthcare professional that an initial risk, prediction, or score of a likelihood to develop a substance use disorder is not available, at which point, the healthcare professional may decide to input another sample for analysis.

In response to a determination that the sample includes the one or more allelic variants, the method 300, at step 316, may further determine, via the trained stacked model 100, a score or other indicator that informs a patient's risk of a substance use disorder. In other words, the SNP profiles of the allelic variants may be input into the trained stacked model 201 or applied to the model classifiers, resulting in an output (e.g., 0 to 1 or some other range of numbers). Further, the score or prediction may be compared to a threshold. As noted, the threshold may be pre-determined or input into the computing device 202. If the score or prediction is less than the threshold, at step 318, a score, prediction, and/or indicator indicating no or low potential or likelihood for development of a substance use disorder by a patient may be returned or transmitted to the user device 220. Additionally, a recommendation for a treatment regimen may be sent to a healthcare professional, based on the determination that there is no or low risk for substance use disorder.

In response to a determination that the score indicator is greater than a threshold, at step 320, a score, prediction, and/or indicator indicating a potential or likelihood for development of a substance use disorder by a patient may be returned or transmitted to the user device 220. Additionally, the method 300 may include identifying one or more associated recommendations related to the determined score, prediction, and/or indicator, and automatically transmitting (along with the score or prediction) the determined initial risk and the one or more associated treatment regimen recommendations (e.g., a recommendation to utilize an alternate drug or prescription, such as a non-opioid, or a reduced dose opioid drug-based treatment regimen) to the user device 220 or display 216 of a healthcare professional via the electronic communication network in real time or in a timeframe of hours to days. Thus, the healthcare professional may have relevant information on treatment regimens to discuss with the patient, and the treatment regimens would be based on a potential for or risk of developing a substance use disorder and/or the treatment regimen recommendation. The method 300 may further include updating the EMR of the patient with further clinical data or patient history and updating the prediction of the initial risk of substance use disorder to reflect the additional clinical data or patient history (e.g., updating the EMR at the patient record database 224).

FIGS. 3B-3E illustrate a flowchart of a method 322 to utilize a stacked machine learning model to predict a subject's or patient's predisposition to substance use disorder (in other words, a patient's risk of developing a substance use disorder), according to another embodiment. In such embodiments, at step 324, a healthcare professional may initiate the method 322 prior to an operation (e.g., pre-operation) to determine a pain management regimen for the patient post-surgery. In another example, method 322 may be initiated by a healthcare professional at an appointment or while performing an annual wellness check (e.g., a wellness check for employment or work-related insurance or pharmaceutical insurance purposes or at the request of a subject/patient's insurer). Further, the initiation may be in response to a determination that the patient requires a prescription of a particular drug or that the patient or a healthcare professional has requested the determination of the patient's risk of developing a substance use disorder. In an embodiment, a healthcare professional may initiate the method 322 when a patient requests an elective procedure.

In response to an initiation of method 322, the computing device 202 may determine whether any prior scores for a particular patient have been determined. In other words, the computing device 202 may determine whether a patient's genetic data has been utilized in the process to determine the risk of developing a substance use disorder. In such examples, the computing device 202 include an input/output connected to a patient record database 224. The computing device 202 may determine whether the prior scores are stored in the patient record database 224 (e.g., in a patients EMR), in a prescription drug monitoring program (PDMP) database or computing device, and/or in another data storage location.

If a patient does not have prior scores available, the computing device 202, at step 328, requests a biological sample, genetic data, and/or physical or clinical data of the patient for analysis or data input at the user device 220. The request may be transmitted to a healthcare professional. The prompt may be displayed via the display 216 of a user device 220. In another example, the sample (e.g., genetic information from a DNA or RNA from a buccal swab) may be input into a SNP analyzer 222 (for example, via a biofilm chip) and the data output from the SNP analyzer 222 may be transmitted to the computing device 202. In yet another example, the computing device 202 may include the functionality of the SNP analyzer 222. In another example, the computing device 202 may prompt or initiate shipment of a home swab kit to the patient. The computing device 202, at step 330, analyzes the sample to determine the SNP profiles of the set of specified allelic variants. The computing device 202 may analyze the biological sample or other genetic material or pre-process the physical or clinical data. In response to the analysis of the SNP profiles of the set of specified allelic variants or receipt of analytical data from the swab or other genetic material and/or in response to the pre-processing of the physical or clinical data, the computing device 202 may initiate the determination of the score indicating the risk of developing use disorder, as described in FIGS. 3A and 3B (e.g., at steps 312 through 320 or steps 304 through 320).

In response to a determination that the score indicating the risk of developing substance use disorder is less than the threshold, at step 332, the computing device 202 may generate a report. The report may include the allelic variants of the patient, the score determined from the trained ensemble or trained stacked model 201, the level of risk associated with developing substance use disorder based on the score, a treatment regimen recommendation, and/or physical or clinical data. In another example, in response to a determination that the score indicating the risk of developing use disorder is more than the threshold, at step 334, the computing device 202 may generate a report as well, with similar information as described above for step 332.

In response to the generation of the report indicating a high risk of developing substance use disorder, the computing device 202 may transmit the report to the PDMP as in step 336. In such examples, a patient's physical or clinical data, along with the patient's predisposition to developing a substance use disorder, may be uploaded from the report to a state or a federal PDMP. Further, the current prescription may be uploaded to the state or a federal PDMP. Thus, doctors, nurses, or other users who may not utilize methods 300, 322, and 342, may determine whether a patient is more or less likely to develop a substance abuse disorder based on the data in the PDMP.

At step 338, the computing device 202 may transmit a treatment regimen recommendation based on the report or based on the score indicative of the level of risk associated with developing substance use disorder. In an embodiment, the report may include the original prescription and the score or indicator for a patient's likelihood or predisposition to develop a substance use disorder. Based on the returned score indicating a high risk of developing a substance use disorder, the computing device 202 may provide suggestions or recommendations for a treatment regimen or possible alterations to the prescription to a drug that may reduce the patient's likelihood to develop the substance use disorder (e.g., suggesting an alteration to a prescription from an opioid based drug to a non-opioid based drug based on the determined likelihood a patient may develop a SUD).

At step 340, the computing device 202 may transmit the report and/or treatment regimen recommendation to patient data storage or a patient's EMR (e.g., patient record database 224). In another example, a field associated with likelihood to develop substance abuse disorder may be altered or updated, based on the results described above. For example, the computing device 202 may include or add a note or indication of the high risk of developing a substance use disorder in the patient's EMR (e.g., stored medical records at a patient record database 224 or other data storage locations).

Figure 3D:
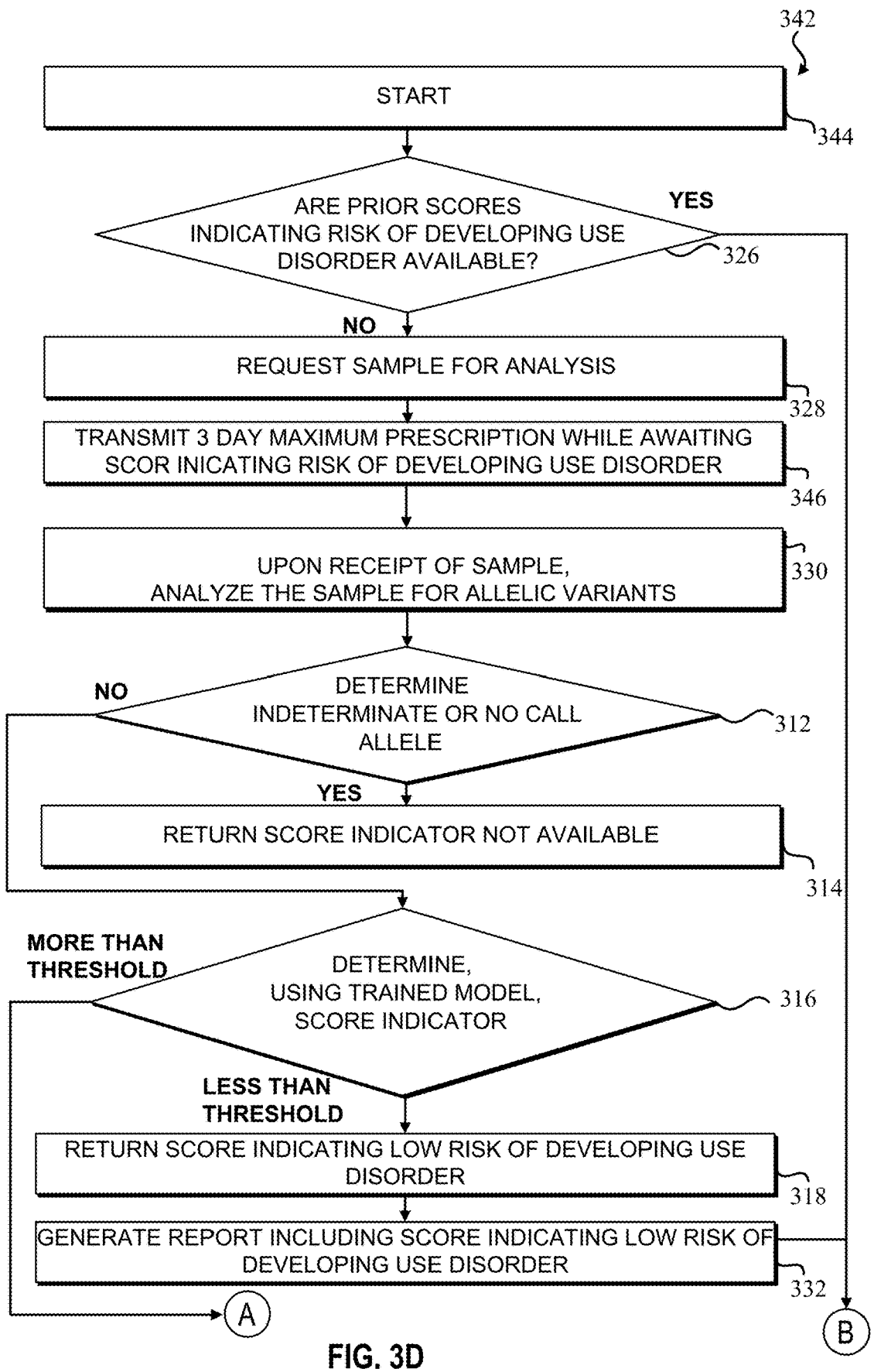
Figure 3E:
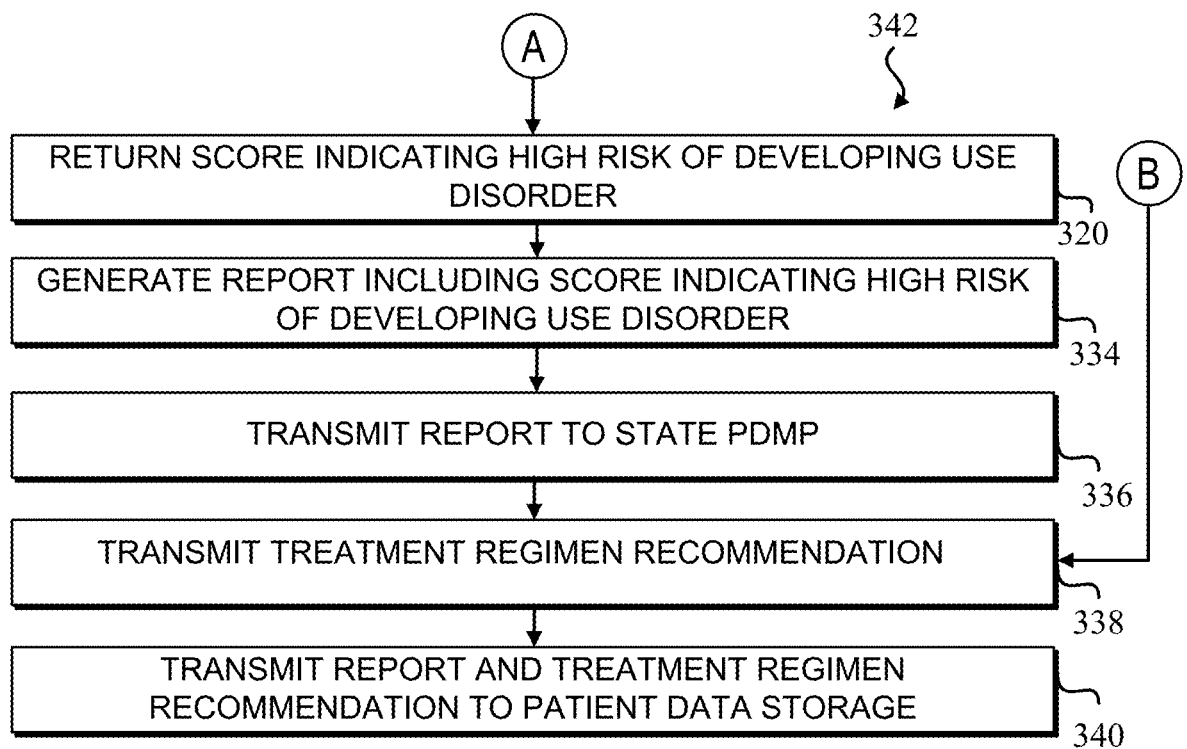

In FIGS. 3D through 3E, the method 342 may be initiated, at step 344, in addition to what is described above for method 322, by a pharmacy benefit manager (PBM) or by an insurer (e.g., prescription drug insurance provider). In such examples, prior to funding or paying for a portion of or all of a certain prescription drug, a PBM or insurer may request that a patient provide a report or score indicating the risk of the patient developing a substance use disorder (as described above). As such a determination may take time, in some examples, the computing device 202, PBM, or insurer may provide a 3-day maximum prescription of the drug prescribed, at step 346. At step 330, in response to receipt of the sample from the patient, the computing device 202 may perform an analysis to obtain one or more SNP profiles of the allelic variants or other patient related information and then initiate the determination of the score indicating the risk of developing use disorder, as described in FIG. 3A (e.g., at steps 312 through 318 or steps 302 through 318). Further, once the score is determined, the computing device 202 may generate reports, transmit the report or update the PDMP as in step 336, recommend possible alterations to a prescription, generate a treatment regimen recommendation, and/or transmit or store the report and prescription data to the patient data storage (e.g., patient record database 224) as described above for FIGS. 3B through 3C (e.g., at steps 332 through 340).

As used herein, an electronic communications network may be any type of network configured to provide communications between components of system 200—the user device 220 or user interface, the SNP analyzer 222, the patient record database 224, and the processor 204 that executes the trained ensemble or trained stacked model 100. For example, the electronic communications network may include a network infrastructure that facilitates the exchange of information and provides communication, such as the Internet, a Local Area network (LAN), wired network, cable, Wireless Local Area Network (WLAN), cellular, satellite, or other suitable connections that enable the exchange of information between the components of systems, as will be readily understood by one having ordinary skill in the art. In some other embodiments, however, the components of the system 200 may be connected through a dedicated direct communication link.

As used herein, a "machine readable storage medium" may be any electronic, magnetic, optical, or other physical storage apparatus to contain or store information such as executable instructions, data, and the like. For example, any machine-readable storage medium described herein may be any of random access memory (RAM), volatile memory, non-volatile memory, flash memory, a storage drive (e.g., hard drive), a solid state drive, any type of storage disc, and the like, or a combination thereof. As noted, the machine-readable storage medium 206 may store or include instructions executable by the processor 204.

The processor 204 or processing resource that executes the trained ensemble or trained stacked model 100 can include a server, storage services, cloud provided by an entity such Microsoft Azure™ or Amazon Web Services® cloud, among others, as will be readily understood by one having ordinary skill in the art. The processor or processing resource may also include a plurality of computing devices in communication with the electronic communications network. For example, in some embodiments, the processor may be a plurality of processors connected together in communication with the electronic communications network. In other embodiments, the processor may be a group of graphical processing units configured to work in parallel as a GPU cluster. A processor may include a single processor device and/or a plurality of processor devices (e.g., distributed processors). A processor 204 may be any suitable processor capable of executing/performing instructions. A processor 204 may include a central processing unit (CPU) that carries out program instructions to perform the basic arithmetical, logical, and input/output operations required to execute the method of predicting risk of substance use disorders or for providing decision support to healthcare professionals to implement a treatment regimen. A processor 204 may include code (e.g., processor firmware, a protocol stack, a database management system, an operating system, or a combination thereof) that creates an execution environment for program instructions. Processes and logic flows described herein may be performed by one or more programmable processors executing one or more computer programs to perform functions by operating on input data and generating corresponding output. The processor is communicatively connected to one or more patient record databases through the electronic communication network. Patient record databases 224 may include one or more memory devices that store information and are accessed and managed through or by the processor 204. For example, databases may include Oracle™ database or other relational databases or non-relational databases such as Hadoop. Databases can include computing components such as database server configured to receive and process requests for data stored in memory devices of databases and to provide data from the databases. The patient record databases 224 may be located remotely, such as in a different geographical location or the cloud. The patient record databases 224 may include EMR of the patients, training data, and/or initial and updated predictive models. The patient record databases 224 may include other clinical data such as age, sex, race, and ethnicity. In an embodiment, the clinical data includes demographic data, socioeconomic data, and any data that about a subject that can be obtained by observation or oral or written communication.

Data encryption may be used to comply with business or regulatory rules, such as Health Insurance Portability and Accountability Act (HIPAA) privacy rules or the like. Such data encryption may ensure a secured communication of the determined initial diagnosis and the one or more associated recommendations between the user device and the third parties, thereby preventing the privacy of the communicated data to be compromised.

Disclosed herein are embodiments of methods of evaluating various substance use disorder risks of a subject, such as opioid use disorder (OUD), alcohol use disorder (AUD), cocaine use disorder (CUD), cannabinoid use disorder (CAUD), and/or nicotine use disorder (NUD). An embodiment includes a multi-variant genetic test of evaluating an OUD, AUD, CUD, NUD, and/or CAUD risk of a subject or patient. Opioids used by a subject can be one or more of any chemicals that interact with opioid receptors on nerve cells in the body, including but not limited to illegal drugs such as heroin, synthetic opioids such as fentanyl, and prescription pain relievers, such as oxycodone (OxyContin®), hydrocodone (Vicodin®), codeine, morphine, and other. Alcohol used by a subject can be one or more of any chemicals that interact with alcohol receptors on nerve cells in the body, including but not limited to legal drugs such as wine, beer, malt liquor, and liquor. Cocaine used by a subject can be one or more of any chemicals that interact with various receptors on nerve cells in the body, including but not limited to illegal drugs such as cocaine and cocaine derivatives. Cannabis used by a subject can be one or more of any chemicals that interact with various receptors on nerve cells in the body, including but not limited to illegal and legal drugs such as cannabis or other substances including tetrahydrocannabinol. Nicotine used by a subject may be one or more of any chemicals that interact with various receptors on nerve cells in the body, including but not limited to legal drugs such as tobacco (included in products, such as cigarettes, cigars, chewing tobacco, or snuff), liquid nicotine (included in products, such as electronic cigarettes), or other forms of nicotine (for example, nicotine patches, lozenges, gum, or other dissolvable products).

To address the role of genetic variability as a screening method for OUD risk, a novel multi-variant genetic test was previously evaluated in a small case cohort study that included 37 patients with a known addiction to prescription opioids or heroin, 30 age- and gender-matched subjects with no known addiction to prescription opioids or heroin, and 138 additional subjects assessed for generalizability. Using a panel of single nucleotide polymorphisms (SNPs) that have been associated with brain pathways that regulate reward together with a computer learning model, a predictive algorithm was developed to estimate OUD risk. The model yielded results suggesting that the algorithm could be used with 97% certainty to identify individuals with low likelihood of developing opioid addiction, and 88% certainty to identify individuals with high likelihood of developing opioid addiction.

A subsequent study was conducted using genetic samples from a large cohort of subjects previously studied with respect to OUD that were provided by the National Institute on Drug Abuse (NIDA) Genetics Consortium (NGS), both to substantiate the earlier findings and develop an ensemble model. In this case study, the National Institute on Drug Abuse provided genetic samples from a large cohort of subjects previously studied for opioid use disorder (OUD). This case study utilized a larger data set and advanced machine learning to build a model that more accurately predicts OUD risk based on genotype alone (i.e., expression of alleles associated with reward, self-control, and affect) or in combination with clinical data (i.e., sex, age, and other substance abuse or dependence). Genetic data was modeled with and without clinical data using a machine learning platform that utilized a random forest model 105, a gradient boosted tree model 107, an elastic net model, a SVM model 109, or some combination thereof. Training and 20-fold cross-validation were performed with 80% 116 of randomly selected samples of the training data 102. Predictive accuracy of the model was assessed in a holdout analysis of 20% 118 of the training data 102. A microarray of 15 single nucleotide polymorphisms (SNPs) associated with risk for opioid addiction was developed.

The machine learning model (or stacked model 210) was trained using data from 77 patients with prescription opioid or heroin addiction and 76 age- and gender-matched subjects with no known addiction to prescription opioids or heroin who had participated in the previous study. The resulting model was then tested on genomic DNA samples from human subjects who had participated in two genome-wide association studies (GWAS) (the Lachman study, nidagenetics.org/studies/study-14-genome-wide-analysis-addiction-susceptibility-genes, and the Nelson study, nidagenetics.org/studies/study-18-opioid-dependence-candidate-genes-and-g-x-e-effects). The NIDA Center for Genetic Studies provided the DNA samples and the subjects' baseline demographic and clinical data, including information regarding substance abuse or dependence on non-opioid substances. Subjects in the Lachman study were recruited from methadone maintenance treatment programs in the New York City metropolitan area and met DSM-IV criteria for opioid dependence, as confirmed by the Structured Clinical Interview for DSM-IV. Subjects, with no known addiction to prescription opioids or heroin, in the Nelson study were recruited from geographic areas in proximity to clinics providing opioid replacement therapy in the greater Sydney, Australia, region, but had themselves used opioids recreationally fewer than 10 times. Participants in both studies provided written informed consent (which allowed for subsequent use of genetic samples), and all procedures in this study were performed in accordance with the informed consent.

Genomic DNA samples were genotyped by AutoGenomics, Inc. (Carlsbad, Calif., USA) using their INIFINITI® PLUS microarray platform and Neural Response Panel of 15 SNPs associated with risk for opioid addiction. Sanger sequencing confirmed>99.9% concordance with SNP genotyping. The potential importance of these SNPs on predicting opioid addiction was analyzed using a probabilistic model, with normalization based on the SNP with the highest relative predictive importance.

Data from the two NIDA studies were modeled using a proprietary platform comprising a random forest model 105, a gradient boosted tree model 107, and elastic net classifier (for example, a SVM model 109). Each trained model produced a classifier. When information from a biological sample 101 is applied to each classifier, a prediction score or other indicator is the output (for example, a value between 0 and 1). The predictions from each classifier were combined by ensemble learning techniques, where multiple sets of predictions from the classifiers have the same dependent variable and the same or similar independent variables. In another example, the predictions or output from the classifiers may be averaged 112 to produce a prediction score 114.

All data processing was conducted under fully blinded conditions, with One-Hot Encoding or Ordinal Encoding used to transform continuous variables into discrete categories. The only major assumption was that model training data are representative of the future scoring data.

Various combinations of the following data were considered and preliminarily tested: genetics, age, sex, and abuse or dependence on other substances (i.e., nicotine, alcohol, cannabinoids). Based on preliminary findings, the ensemble (blended or stacked) model was developed and deployed using genetic data only and genetic plus clinical data. As OUD cases are rare relative to the overall general population, an under-sampling method was used in which the number of samples in the rare class was matched to an approximately similar number of samples from subjects with no known addictions. Twenty-fold cross-validation was performed with 80% 116 of randomly selected samples used for training/learning and 20% 118 of the samples were used for holdout analysis.

Confusion matrix outputs were as follows: (i) F1 score, which measures accuracy based on precision and recall (F1=2*precision*recall/(precision+ recall)), in which precision is the number of correct positive results divided by the number of all positive results returned by the model, and recall is the number of correct positive results divided by the number of samples that should have been identified as positive; (ii) true positive rate (sensitivity); (iii) false positive rate; (iv) true negative rate (specificity); (v) false negative rate; (vi) positive predictive value (percentage of all positive predictions that were correct); (vii) negative predictive value (percentage of all negative predictions that were correct); (viii) accuracy (percentage of all correctly classified instances), and (v) Matthews Correlation Coefficient, which measures model quality when the data set is unbalanced. Additional outputs included: prediction distribution graphs, which illustrate how well the model discriminates between prediction classes; lift charts, which depict how well a model segments the target population and predicts the target outcome; and receiver operating characteristic (ROC) curves, which plot true positives against false positives with greater area under the curve (AUC) indicating better accuracy.

Genomic samples and clinical data from 458 cases and 508 cases with no known addiction to prescription opioids or heroin were analyzed. GWAS included genomic samples from 1181 subjects, 663 cases from the Lachman study and 518 cases with no known addiction to prescription opioids or heroin from the Nelson study. To identify likely cases of OUD per DSM-5 criteria, 215 subjects were excluded from analyses based on the following criteria: cases that were identified as positive for both opioid dependence and opioid abuse (n=136); cases with no known addiction to prescription opioids or heroin and 1 case that were positive for opioid abuse only (n=13); or insufficient information (n=66).

In the remaining analysis set (N=966), 458 subjects from the Lachman study were classified as positive for OUD per DSM-5 criteria and 508 (2 from the Lachman study and 506 from the Nelson study) were classified as negative for OUD. Baseline demographic and clinical data for the analysis set are shown in Table 1.

TABLE 1

Baseline Demographics and Clinical Data

| Variable | Case Subjects (N = 458) | Subjects with No Known Addiction (N = 508) |
|---|---|---|
| Mean age (SD) - year | 42.0 (7.6) | 35.0 (10.6) |
| Female sex - no. (%) | 201 (43.9) | 283 (55.7) |
| Race or ethnic group - no. (%) | | |
| White non-Hispanic | 47 (10.3) | 360 (70.9) |
| Black non-Hispanic | 110 (24.0) | 1 (0.2) |
| Hispanic | 291 (63.5) | 1 (0.2) |
| Other | 10 (2.2) | 122 (24.0) |
| Unknown | | 24 (4.7) |
| Substance abuse or dependence - no. (%)* | | |
| Alcohol abuse | 45 (9.8) | 106 (20.9) |
| Alcohol dependence | 194 (42.4) | 134 (26.4) |
| Nicotine dependence | NA | 204 (40.2) |
| Cannabis abuse | 38 (8.3) | 65 (12.8) |
| Cannabis dependence | 249 (54.4) | 135 (26.6) |

*Per DSM-IV criteria

DSM-IV, *Diagnostic and Statistical Manual of Mental Disorders*, 4th Edition;

NA, not available

Among the 15 SNPs included in the Neural Response Panel, a genetic polymorphism in the serotonin receptor gene (rs7997012) had the highest probability of being individually associated with opioid addiction and was therefore assigned a normalized impact score of 1.0 (Table 2). Other SNPs that had relatively high individual probabilities of being associated with opioid addiction were for polymorphisms located in genes encoding galanin (rs948854) and the ATP-binding cassette (ABC) transporter (rs1045642), with normalized impact scores of 0.7562 and 0.6910, respectively. Deployment of the previously developed algorithm based on only genetics to the 966 subjects included in the NIDA analysis set resulted in a prediction that was 91.5% sensitive (95% CI: 88.5-93.9%), 45.1% specific (95% CI: 40.7-49.5%), and 67.1% accurate (95% CI: 64.0-70.0%), with AUC=0.7000.

TABLE 2

Normalization of Genetic Variants

| | | | Impact | |
|---|---|---|---|---|
| SNP ID | Gene | Gene Description | Unnormalized | Normalized |
| rs7997012 | 5-HTR2A | Serotonin 2A receptor | 0.0797 | 1.0 |
| rs948854 | GAL | Galanin | 0.0603 | 0.7562 |
| rs1045642 | ABCB1 | ATP binding cassette transporter 1 | 0.0551 | 0.6910 |
| rs4680 | COMT | Catechol-O-methyltransferase | 0.0446 | 0.5591 |
| rs6347 | DAT1 | Dopamine transporter | 0.0432 | 0.5423 |
| rs1800497 | DRD2 | Dopamine D2 receptor | 0.0331 | 0.4157 |
| rs4532 | DRD1 | Dopamine D1 receptor | 0.0276 | 0.3455 |
| rs1801133 | MTHFR | Methylene tetrahydrofolate reductase | 0.0232 | 0.2909 |

TABLE 2-continued

Normalization of Genetic Variants

| SNP ID | Gene | Gene Description | Impact Unnormalized | Normalized |
|---|---|---|---|---|
| rs1611115 | DBH | Dopamine beta hydroxylase | 0.0210 | 0.2628 |
| rs2236861 | DOR | Delta opioid receptor | 0.0197 | 0.2473 |
| rs1799971 | OPRM1 | Mu opioid receptor | 0.0113 | 0.1419 |
| rs3758653 | DRD4 | Dopamine D4 receptor | 0.0111 | 0.1397 |
| rs211014 | GABA | Gamma-aminobutyric acid | 0.0100 | 0.1250 |
| rs1051660 | OPRK1 | Kappa opioid receptor | 0.0079 | 0.0990 |
| rs9479757 | MUOR | Mu opioid receptor | 0.0029 | 0.0367 |

Figure 4:
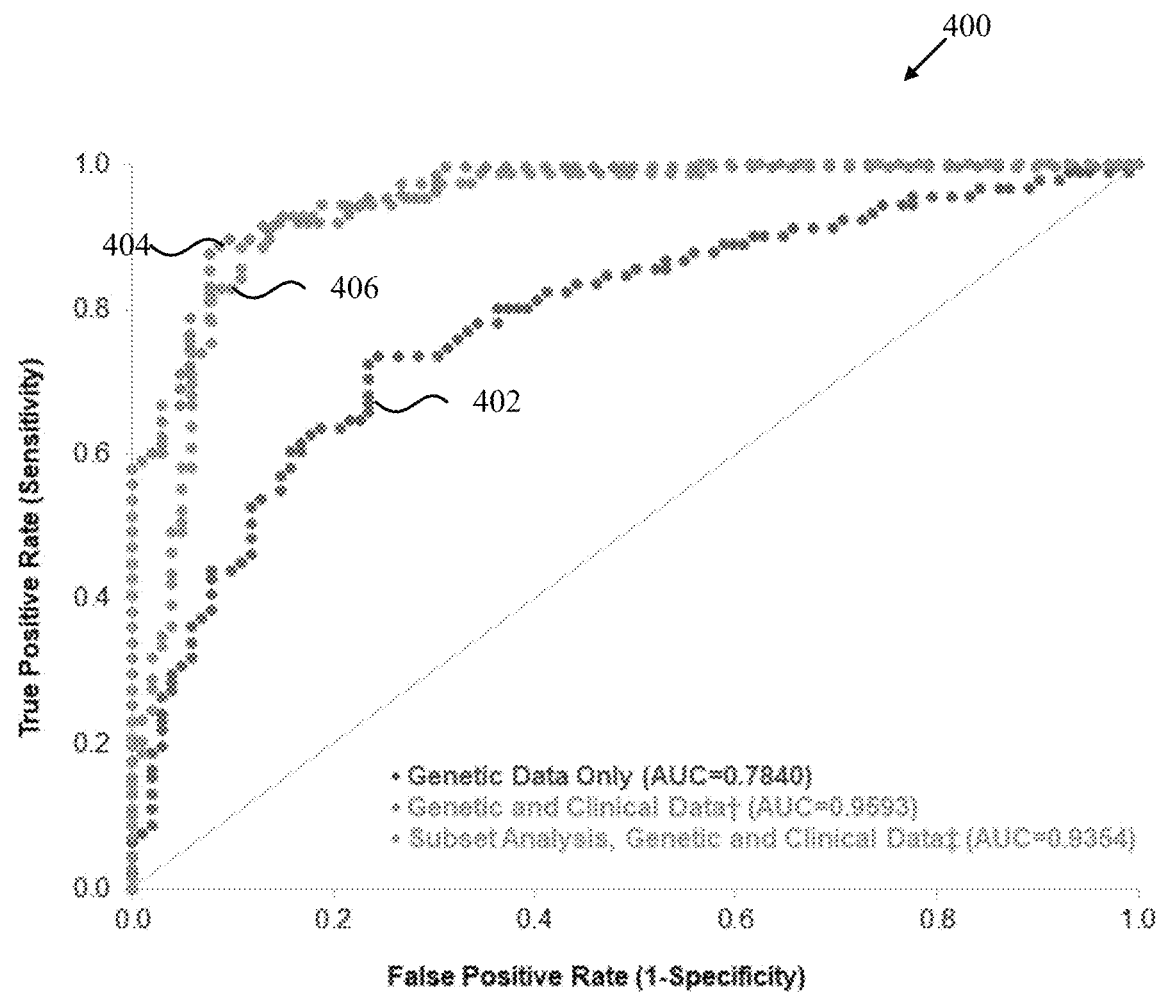
FIG. 4 is a representation of the receiver operating characteristic curves using (i) genetic data only, (ii) genetic data and clinical data, and (iii) genetic data and a subset of clinical data, according to an embodiment of the present disclosure.
Figure 5A:
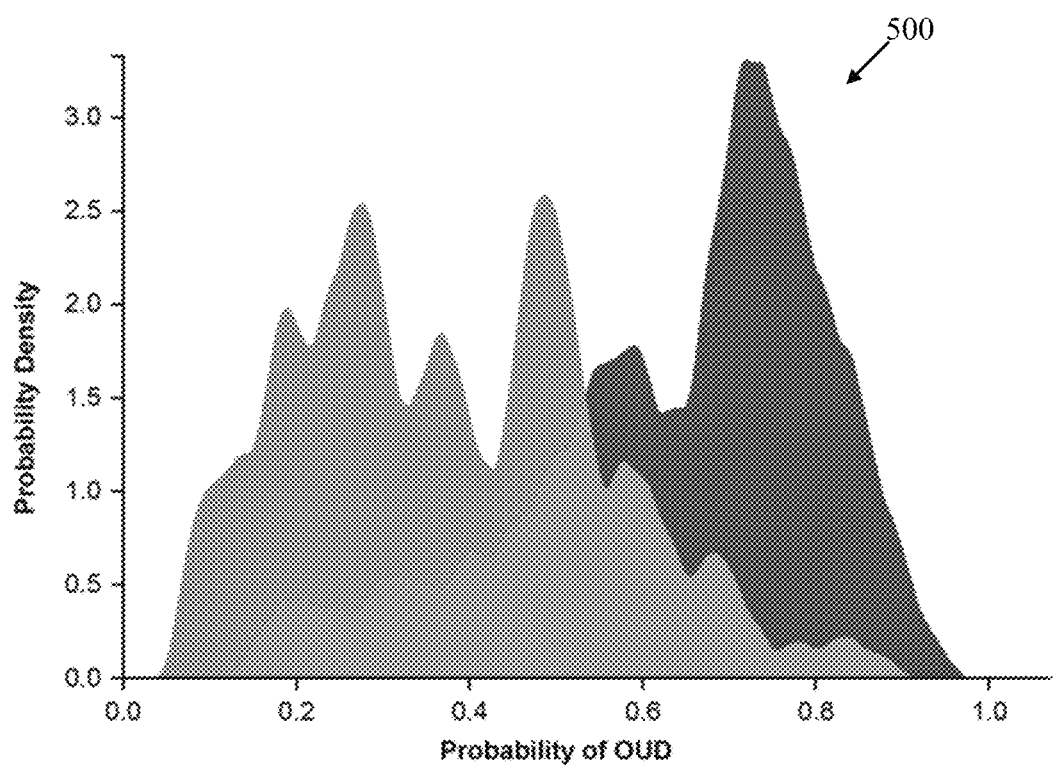
FIGS. 5A and 5B are graphical representations of the prediction distribution based on genetic data only and a combination of genetic data and clinical data, respectively, according to an embodiment of the present disclosure.
Figure 5B:
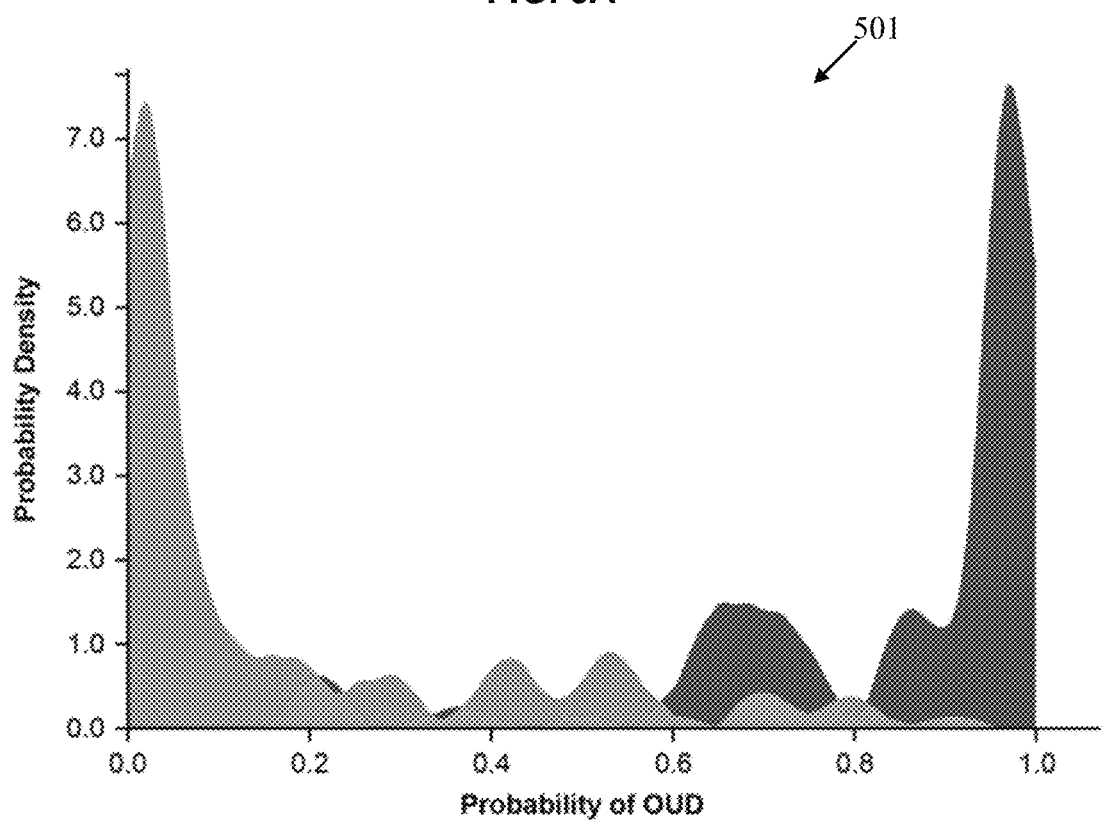
Figure 6A:
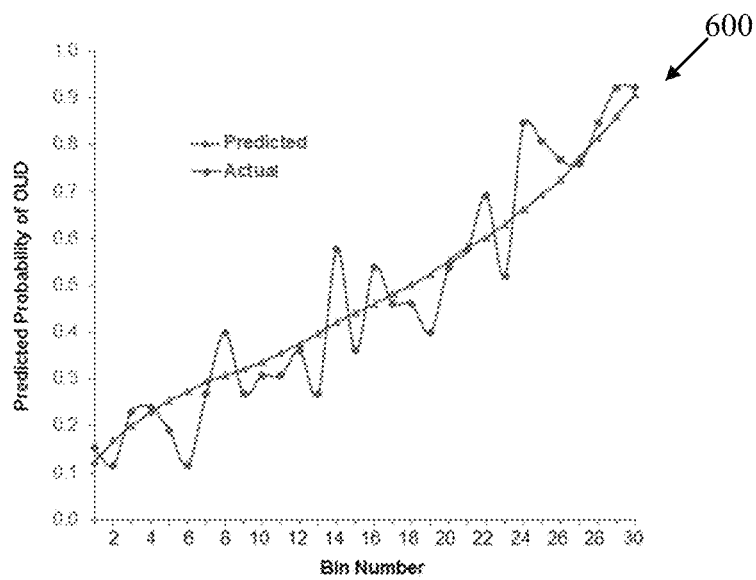
FIGS. 6A and 6B are lift charts of the ensemble predictive model developed by using genetic data only and a combination of genetic data and clinical data, respectively, according to an embodiment of the present disclosure.
Figure 6B:
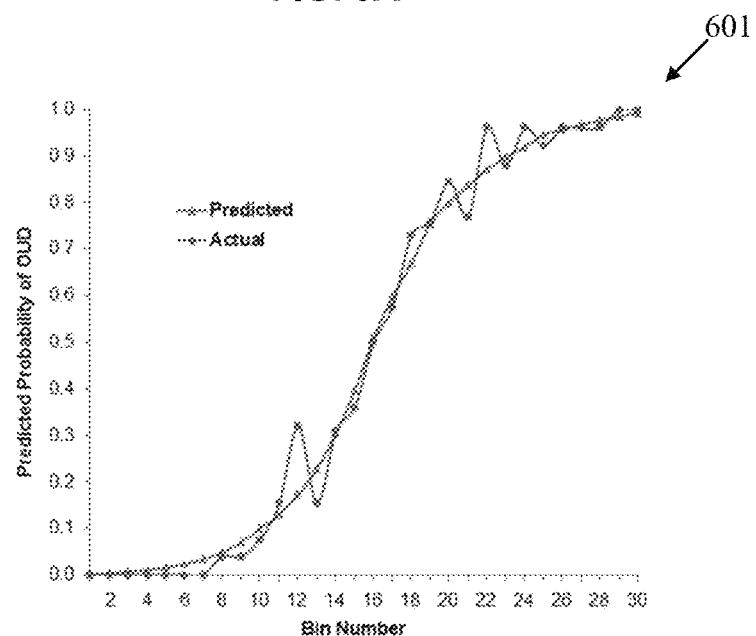

Deployment of the trained ensemble or trained stacked model 100 developed using the analysis set of 966 cases and cases with no known addiction to prescription opioids or heroin including only genetic data yielded a prediction that was 73.6% sensitive (95% CI: 63.4-82.3%), 75.5% specific (95% CI: 66.0-83.5%), and 74.6% accurate (95% CI: 67.9-80.6%), with AUC=0.7840 (Table 3; FIG. 4). FIG. 4 is a representation 400 of the receiver operating characteristic curves using (i) genetic data only 402, (ii) genetic and clinical data 404, and (iii) genetic and a subset of clinical data 406, according to an embodiment of the present disclosure. FIGS. 5A and 5B are graphical representations 500, 501 of the prediction distributions based on genetic data only and genetic and clinical data, respectively. The prediction distribution graph indicated moderate discrimination between cases and cases with no known addiction to prescription opioids or heroin (FIG. 5A).

without the ensemble predictive model. Lift charts are visual representations of model performance. Lift charts showed a close fit between predicted and actual values, and the area under the ROC curves indicated that a high proportion of the predictions could be classified as true (FIGS. 4 and 6A-6B; Table 3). FIGS. 6A and 6B are lift charts of the ensemble predictive model developed by using genetic data only 600 and a combination of genetic and clinical data 601, respectively, according to an embodiment of the present disclosure. Deployment of the model using clinical data alone demonstrated approximately 50% predictive accuracy.

Upon observing the mismatch in age between the case and cases with no known addiction to prescription opioids or heroin datasets, the model was deployed using the genetic and clinical variables without including age. In this analysis, predictive accuracy was slightly diminished with 76.9% sensitivity (95% CI: 66.9-85.1%), 76.5% specificity (95%

TABLE 3

Performance of Ensemble Model on Holdout Analysis

| Metric | Genetic Data Only | Genetic + Clinical† Data | Subset Analysis Genetic + Clinical‡ Data |
|---|---|---|---|
| F1 score | 0.7322 | 0.8962 | 0.8690 |
| True positive (sensitivity) | 0.7363 | 0.9011 | 0.9130 |
| False positive | 0.2451 | 0.0980 | 0.1287 |
| True negative (specificity) | 0.7549 | 0.9020 | 0.8713 |
| Positive predictive value | 0.7283 | 0.8913 | 0.8289 |
| Negative predictive value | 0.7624 | 0.9109 | 0.9362 |
| Accuracy | 0.7461 | 0.9016 | 0.8882 |
| Matthews correlation coefficient | 0.4909 | 0.8026 | 0.7747 |
| AUC | 0.7840 | 0.9593 | 0.9354 |

†Clinical data includes age, sex, nicotine and/or alcohol abuse or dependence, cannabinoid abuse or dependence, and no illicit drug use.
‡Subset analysis excludes African-American subjects. Clinical data includes age, sex, nicotine and/or alcohol abuse or dependence, cannabinoid abuse or dependence, and no illicit drug use.
AUC, area under the receiver operating characteristic curve Models that included both genetic and clinical data showed increased predictive accuracy for OUD risk (FIG. 5B). The prediction from the model that included age, sex, and abuse or dependence on other substances was 87.9% sensitive (95% CI: 79.4-93.8%), 73.5% specific (95% CI: 63.9-81.8%), and 80.3% accurate (95% CI: 74.0-85.7%), while including the additional clinical variable of "no illicit drug use" to the model resulted in prediction that was 90.1% sensitive (95% CI: 82.0-95.4%), 90.2% specific (95% CI: 82.7-95.2%), and 90.2% accurate (95% CI: 85.0-94.0%), with AUC=0.9593 (Table 3; FIG. 4). The prediction distribution graph indicated considerable discrimination between cases and cases with no known addiction to prescription opioids or heroin (FIG. 5B). Lift charts provide a measure of the effectiveness of the ensemble predictive model and are calculated as the ratio between the results obtained with and CI: 67.0-84.3%), and 76.7% accuracy (95% CI: 70.1-82.5%). Similarly, to account for potential differences in allele frequencies among different racial/ethnic groups, the model was deployed using the genetic and clinical variables on a subset of cases (n=348) and cases with no known opioid (n=507) that did not include African-American subjects (the only racial/ethnic group in which minor allele frequencies reported in dbSNP for a number of the SNPs included in the Neural Response Panel differ significantly from other racial ethnic groups). This analysis resulted in prediction that was 91.3% sensitive (95% CI: 82.0-96.7%), 87.1% specific (95% CI: 79.0-93.0%), and 88.8% accurate (95% CI: 83.1-93.1%), with AUC=0.9394 (Table 3, FIG. 4). These findings were similar to the results observed in the full case cohort.

Results of the current study demonstrate that risk for opioid addiction can be predicted by a panel of SNPs associated with the brain's reward pathways, and that prediction sensitivity, specificity, and accuracy can be improved by including clinical data such as age, sex, and abuse or dependence on other substances in the predictive algorithm. The study demonstrated that use of ensemble machine learning to search for the best set of models (blended or stacked), based on both the characteristics of the data and the prediction target increases the predictive accuracy of the derived algorithm. This study confirmed the findings of an earlier study in a much larger case cohort.

This affordable, non-invasive or minimally invasive tool for risk assessment for opioid addiction or OUD provides decision support for implementing treatment regimens. For individuals prospectively identified as genetically at-risk for OUD, a treatment regimen may avoid or reduce opioid exposure, even in the context of perioperative pain management. The treatment regimen for such an individual would be involve non-opioid modalities, such as regional anesthesia and analgesic techniques, and multimodal analgesia. Additionally, knowledge regarding the genetic predisposition for OUD informs treatment paradigms for at-risk individuals who have been exposed to opioids, as such individuals may be candidates for buprenorphine-assisted dose reduction or behavioral interventions. A highly reliable risk assessment tool can provide improved access to opioid pain medications for individuals with legitimate medical needs, who are at low risk for addiction, but who currently are being denied adequate pain management, or are having difficulty accessing primary care.

While a genetic component to the pathogenesis of opioid addiction is generally well accepted, GWAS to identify candidate genes and their associated SNPs have often not been replicated or have shown inconsistent results. The SNPs selected for use in the polygenetic panel described in this study were based on published literature, and it may be the case that individual SNPs that fail to achieve a statistically significant association with opioid addiction in GWAS may not be causal but closely linked to addiction risk. There remains the difficulty of tying the SNP panel used in this study to the underlying neurobiology of opioid addiction, however, the SNP panel is clearly a crucial factor in the model. While certain clinical characteristics (e.g., older age, female sex) appear to be associated with longer term opioid use, clinical characteristics alone were not predictive in this model; without the genetic component, the predictive accuracy of the model declined to approximately 50%.

In the Lachman study approximately two-thirds of subjects were Hispanic and one-quarter were African-American, while 70% of subjects in the Nelson study were White. While frequencies of alleles are slightly different between racial and ethnic groups, the current study cannot determine whether these dissimilarities are related to ethnic differences or are disease-related. However, the subset analysis that excluded African-American subjects yet showed the model retained a high level of predictive accuracy suggests that racial/ethnic allelic frequency differences do not affect the model described here. Nonetheless, additional studies that control for ethnicity are in progress. Additionally, it was observed that including age as a variable in model development appeared to increase its predictive accuracy, however it is not clear whether age is a true signal of risk or whether it merely reflects increased likelihood of opioid exposure.

Results from this study demonstrate the generalizability of a highly sensitive and specific predictive assay for risk of opioid addiction, which can prevent opioid exposure in at-risk individuals, while at the same time increasing access to legitimately needed opioid medications among individuals suffering from severe and debilitating acute and chronic pain who are at low risk for addiction. Both patients and clinicians can make better informed treatment decisions with knowledge of potential risks for addiction. Risk for opioid addiction can be predicted by a panel of SNPs associated with the brain's reward pathways, and predictive accuracy increases with the inclusion of clinical data. Methods and systems for predicting the risk of opioid addiction inform treatment decisions for the patient.

While many embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A system to select a treatment regimen for addressing a substance use disorder in a subject, the system comprising:
   a SNP analyzer to analyze a sample from the patient and to provide a first plurality of SNP profiles of each of a set of specified allelic variants in the sample; and
   a processor and a machine-readable storage medium storing (i) a machine learning ensemble model, the machine learning ensemble model being trained with inputs comprising a second plurality of SNP profiles associated with the specified set of allelic variants from a first plurality of test subjects and a third plurality of SNP profiles associated with the specified set of allelic variants from a second plurality of test subjects and outputs comprising a first plurality of substance use indicators specifying that the first plurality of test subjects have been diagnosed with the substance use disorder and a second plurality of substance use indicators specifying that the second plurality of test subjects have not been diagnosed with the substance use disorder, and (ii) instructions, when executed by the processor, configured to:
      provide the machine learning ensemble model with the first plurality of SNP profiles to generate a score indicative of risk to a substance use disorder for the patient based on the first plurality of SNP profiles,
      in response to the score based on the first plurality of SNP profiles being greater than a pre-determined threshold;
         transmit to a user interface an output indicating a predisposition of the patient to develop the substance use disorder, and
         transmit a recommendation for low-opioid or non-opioid based treatment regimen including low opioid or non-opioid prescription drugs for administration, and
      in response to the score based on the first plurality of SNP profiles being less than or equal to the pre-determined threshold;
         transmit to the user interface an output indicating a lower likelihood of the patient to develop the substance use disorder and
         transmit a recommendation for an opioid based treatment regimen including opioid prescriptions for administration.

2. The system of claim 1, further comprising:
a database storing the low-opioid or non-opioid based treatment regimen and the opioid-based treatment regimen.

3. The system of claim 1, wherein the machine learning ensemble model is generated by at least one of a random tree model and a support vector machine model.

4. A method of delivering a treatment regimen to address a substance use disorder in a subject, the method comprising:
analyzing a sample of the subject to obtain one or more SNP profiles of each of a set of specified allelic variants;
in response to the one or more SNP profiles of each of the set of specified allelic variants:
determining, via a processor of a computing device and a machine learning ensemble model stored in a machine-readable storage medium of the computing device, a score indicating the subject's risk for developing a substance use disorder based on the one or more SNP profiles of each of the set of specified allelic variants; and
in response to the score indicating a high risk for the subject to develop the substance use disorder, delivering a low-opioid or non-opioid treatment regimen to the subject.

5. The method of claim 4,
wherein the score indicating the subject's risk for developing the substance use disorder is a value from the machine learning ensemble model between 0 and 1,
wherein the machine learning ensemble model includes a pre-determined threshold,
wherein the score being greater than the pre-determined threshold indicates the subject has a higher risk for developing the substance use disorder, and
wherein the score being less than or equal to than the pre-determined threshold indicates the subject has a lower risk for developing the substance use disorder.

6. The method of claim 4, wherein the computing device includes a SNP analyzer to analyze the sample of the subject to obtain the one or more SNP profiles of each of a set of specified allelic variants.

7. The method of claim 4, wherein the method further comprises:
in response to the determination of the score, generating, via the processor, a report, the report including the treatment regimen recommendation and the score.

8. The method of claim 7, wherein the method further comprises:
in response to the generation of the report, transmitting, via the processor, the report to a state prescription drug monitoring program (PDMP) database.

9. The method of claim 4, wherein the method further comprises:
prior to receipt of the sample, determining, via the processor, whether a prior determined score indicating the subject's risk for developing a substance use disorder is available for the subject; and
in response to the determination that the prior determined score is not available for the subject, transmitting, via the processor of the computing device, a request for a sample of the subject;
in response to the determination that the prior determined score is available for the subject, determining, via the processor, a treatment regimen recommendation based on the prior determined score.

10. The method of claim 9, wherein the prior determined score is stored in a patient record database containing electronic health records of the subject.

11. The method of claim 4, wherein the set of specified allelic variants includes one or more of allelic variants of the following genes: serotonin 2A receptor, galanin, ATP binding cassette transporter 1, catechol-O-methyltransferase, dopamine transporter, dopamine D2 receptor, dopamine D1 receptor, methylene tetrahydrofolate reductase, dopamine beta hydroxylase, delta opioid receptor, a first mu opioid receptor (OPRM1), dopamine D4 receptor, gamma-aminobutyric acid, kappa opioid receptor, and a second mu opioid receptor (MUOR).

12. The method of claim 4, wherein the set of specified allelic variants includes allelic variants of the following genes: serotonin 2A receptor, galanin, ATP binding cassette transporter 1, catechol-O-methyltransferase, dopamine transporter, dopamine D2 receptor, dopamine D1 receptor, methylene tetrahydrofolate reductase, dopamine beta hydroxylase, delta opioid receptor, a first mu opioid receptor (OPRM1), dopamine D4 receptor, gamma-aminobutyric acid, kappa opioid receptor, and a second mu opioid receptor (MUOR).

13. The method of claim 4, wherein the determination of the score is further based on a subject's clinical data.

14. The method of claim 4, wherein the non-opioid treatment regimen includes buprenorphine-assisted dose reduction.

15. A system to determine a patient's risk for developing a substance use disorder in a subject, the system comprising a substance use disorder in a subject, the system comprising:
a SNP analyzer to analyze a sample from the patient and to provide a first plurality of SNP profiles of each of a set of specified allelic variants in the sample; and
a processor and a machine-readable storage medium storing (i) a machine learning ensemble model, the machine learning ensemble model being trained with inputs comprising a second plurality of SNP profiles associated with the specified set of allelic variants from a first plurality of test subjects and a third plurality of SNP profiles associated with the specified set of allelic variants from a second plurality of test subjects and outputs comprising a first plurality of substance use indicators specifying that the first plurality of test subjects have been diagnosed with the substance use disorder and a second plurality of substance use indicators specifying that the second plurality of test subjects have not been diagnosed with the substance use disorder, and (ii) instructions, when executed by the processor, configured to:
provide the machine learning ensemble model with the first plurality of SNP profiles to generate a score indicative of risk to a substance use disorder for the patient based on the first plurality of SNP profiles,
in response to the score based on the first plurality of SNP profiles being greater than a pre-determined threshold:
transmit to a user interface an output indicating a predisposition of the patient to develop the substance use disorder, and
in response to the score based on the first plurality of SNP profiles being less than or equal to the pre-determined threshold:
transmit to the user interface an output indicating a lower likelihood of the patient to develop the substance use disorder.

16. The system of claim 15, further comprising:
a database storing a non-opioid based treatment regimen recommendation and an opioid-based treatment regimen recommendation.

17. The system of claim 16, wherein the machine-readable storage medium further has instructions to:
in response to the score based on the first plurality of SNP profiles being greater than the pre-determined threshold, retrieve the non-opioid based treatment regimen recommendation from the database; and
transmit to the user interface an output indicating the predisposition of the patient to develop the substance use disorder and the non-opioid based treatment regimen recommendation.

18. The system of claim 15, wherein the machine learning ensemble model is generated by at least one of a random tree model and a support vector machine model.

* * * * *